(12) United States Patent
Avidor

(10) Patent No.: US 11,083,813 B2
(45) Date of Patent: Aug. 10, 2021

(54) SYSTEM AND METHOD FOR SELECTING AND RELEASING FLAVOR

(71) Applicant: Agan Aroma & fine chemicals Ltd., Ashdod (IL)

(72) Inventor: Yoav Avidor, Tel-Aviv (IL)

(73) Assignee: Agaa Aroma & fine chemicals Ltd., Ashdod (IL)

( * ) Notice: Subject to any disclaimer, the term of this patent is extended or adjusted under 35 U.S.C. 154(b) by 26 days.

(21) Appl. No.: 16/615,430

(22) PCT Filed: May 24, 2018

(86) PCT No.: PCT/IL2018/050576
§ 371 (c)(1),
(2) Date: Nov. 21, 2019

(87) PCT Pub. No.: WO2018/216024
PCT Pub. Date: Nov. 29, 2018

(65) Prior Publication Data
US 2020/0171193 A1   Jun. 4, 2020

Related U.S. Application Data

(60) Provisional application No. 62/510,851, filed on May 25, 2017.

(51) Int. Cl.
*A61L 9/12* (2006.01)
*A61L 9/03* (2006.01)
*A61L 9/14* (2006.01)

(52) U.S. Cl.
CPC ............... *A61L 9/125* (2013.01); *A61L 9/032* (2013.01); *A61L 9/035* (2013.01); *A61L 9/122* (2013.01);
(Continued)

(58) Field of Classification Search
CPC .......... A61L 9/032; A61L 9/035; A61L 9/122; A61L 9/125; A61L 9/14; A61L 2209/11;
(Continued)

(56) References Cited

U.S. PATENT DOCUMENTS

| 5,565,148 A | 10/1996 | Pendergrass, Jr. |
| 6,282,458 B1 * | 8/2001 | Murayama ............... A61L 9/122 422/108 |
| 6,338,818 B2 | 1/2002 | Budman |
| 6,712,287 B1 | 3/2004 | Le Pesant et al. |

(Continued)

FOREIGN PATENT DOCUMENTS

| EP | 0831384 | 3/1998 |
| GB | 2432789 | 6/2007 |

(Continued)

OTHER PUBLICATIONS

Notification of Office Action and Search Report dated Sep. 23, 2020 From the State Intellectual Property Office of the People's Republic of China Re. Application No. 201880046676.0. (9 Pages).

(Continued)

*Primary Examiner* — Timothy C Cleveland

(57) ABSTRACT

A system for releasing flavor comprises: a plurality of compartments adapted to receive a respective plurality of capsules, each capsule containing therein a flavor material; a dispenser system configured for dispensing into an environment a fluid obtained from at least one flavor material; and a controller configured for automatically selecting a dispensing protocol, for signaling the dispenser system to dispense fluids obtained from at least one flavor material contained in at least one capsule of the compartments, and for automatically re-executing the selecting and the signaling, according to a shuffle protocol.

18 Claims, 5 Drawing Sheets

(52) U.S. Cl.
CPC .............. *A61L 9/14* (2013.01); *A61L 2209/11* (2013.01); *A61L 2209/12* (2013.01); *A61L 2209/132* (2013.01); *A61L 2209/133* (2013.01)

(58) Field of Classification Search
CPC ......... A61L 2209/132; A61L 2209/133; A61L 2209/134; A61L 2209/135
See application file for complete search history.

(56) References Cited

U.S. PATENT DOCUMENTS

| | | |
|---|---|---|
| 2010/0243754 A1 | 9/2010 | Harris |
| 2010/0294852 A1 | 11/2010 | Banco et al. |
| 2012/0000989 A1 | 1/2012 | Bordier |

FOREIGN PATENT DOCUMENTS

| | | |
|---|---|---|
| WO | WO 2004/093929 | 11/2004 |
| WO | WO 2016/098114 | 6/2016 |
| WO | WO 2018/216024 | 11/2018 |

OTHER PUBLICATIONS

Translation Dated Nov. 12, 2020 of Notification of Office Action dated Sep. 23, 2020 From the State Intellectual Property Office of the People's Republic of China Re. Application No. 201880046676.0. (6 Pages).

International Preliminary Report on Patentability dated Dec. 5, 2019 From the International Bureau of WIPO Re. Application No. PCT/IL2018/050576. (7 Pages).

International Search Report and the Written Opinion dated Aug. 19, 2018 From the International Searching Authority Re. Application No. PCT/IL2018/050576. (10 Pages).

Supplementary European Search Report and the European Search Opinion dated Feb. 5, 2021 From the European Patent Office Re. Application No. 18806581.7. (8 Pages).

* cited by examiner

SYSTEM AND METHOD FOR SELECTING AND RELEASING FLAVOR

RELATED APPLICATION

This application is a National Phase of PCT Patent Application No. PCT/IL2018/050576 having International filing date of May 24, 2018, which claims the benefit of priority under 35 USC § 119(e) of U.S. Provisional Patent Application No. 62/510,851 filed on May 25, 2017. The contents of the above applications are all incorporated by reference as if fully set forth herein in their entirety.

FIELD AND BACKGROUND OF THE INVENTION

The present invention, in some embodiments thereof, relates to the release of a fluid into the environment and, more particularly, but not exclusively, to a system and method for selecting and releasing flavor.

In any place where people gather there will be various odors, fragrances and the like. It is common for homeowners and businesses to oftentimes struggle to maintain pleasant smelling environments. Many odors from such various things as cooking, personal hygiene products, the presence of pets, and cigarette smoke can be present in a home or business. Odors of these types are often difficult to combat.

Aroma emitting devices are well known and are commonly used in homes and commercial establishments to provide a pleasant atmosphere for people in given areas. Such devices passively or actively transmit aromas to the general surroundings.

Examples of passive devices include air wicks, scented gel-packs, and aromatic sticks resting in a bottle of aromatic liquid and protruding out of the bottle so that the liquid is absorbed and drawn upward through the stick where upon, the liquid evaporates from the surface of the stick. One type of active aromatic device is plugged into an electrical power outlet, whereupon, a small heating element heats an aromatic liquid containing member thus causing the liquid to evaporate and escape into the adjacent surroundings. Another example of an active aromatic device is powered by battery or wall outlet and sprays an aromatic mist periodically into a room.

Aromatic devices are commonly used by individuals who enjoy various selected scents. Further, the use of such aromatic devices has been found to improve or enhance the general demeanor of individuals in a particular surrounding. Certain scents have been found to cause desirable mood changes in people in general.

International Publication No. WO2016/098114 discloses a system for releasing flavor. The system comprises: a plurality of compartments adapted to receive a respective plurality of capsules, each capsule containing therein a flavor material; a dispenser system configured for dispensing into an environment a fluid obtained from at least one flavor material; and a controller configured for receiving data pertaining to a selection of at least two of the compartments and for signaling the dispenser system to dispense fluids obtained from flavor materials contained in capsules of the selected compartments.

SUMMARY OF THE INVENTION

According to an aspect of some embodiments of the present invention there is provided a system for releasing flavor. The system comprises: a plurality of compartments adapted to receive a respective plurality of capsules, each capsule containing therein a flavor material; a dispenser system configured for dispensing into an environment a fluid obtained from at least one flavor material; and a controller configured for automatically selecting a dispensing protocol, for signaling the dispenser system to dispense fluids obtained from at least one flavor material contained in at least one capsule of the compartments, and for automatically re-executing the selecting and the signaling, according to a shuffle protocol.

According to some embodiments of the invention the controller is configured to extract information pertaining to contents of capsules in the containers, and automatically selecting a shuffle protocol based on the information.

According to some embodiments of the invention the system comprises a user interface configured for selecting the shuffle protocol or parameters for the shuffle protocol.

According to some embodiments of the invention the controller is configured for shuffling between dispensing activities with a higher dispensing rate and dispensing activities with a lower dispensing rate.

According to some embodiments of the invention the controller is configured for shuffling between dispensing activities with a higher duration and dispensing activities with a lower duration.

According to some embodiments of the invention the controller is configured for shuffling between dispensing activities with longer pauses between dispensing events and dispensing activities with shorter pauses between dispensing events.

According to some embodiments of the invention the controller is configured for shuffling between mixing ratios, and to control, for each mixing ratio, relative amounts of fluids dispensed from at least two capsules, responsively to the mixing ratio.

According to some embodiments of the invention the control of the amounts is by releasing different fluids over different time durations.

According to some embodiments of the invention the dispenser system comprises a plurality of individually controlled fans or blowers, each generating a flow out of a different compartment, and wherein the control of the amounts is by controlling rotation speeds of the fans or blowers.

According to some embodiments of the invention the controller is configured for automatically selecting a compartment according to the shuffle protocol, and for signaling the dispenser system to dispense fluids obtained from flavor materials contained in a capsule of the selected compartment.

According to some embodiments of the invention the controller is configured for automatically selecting at least two compartments according to the shuffle protocol, and for signaling the dispenser system to dispense fluids obtained from flavor materials contained in capsules of the at least two selected compartments.

According to some embodiments of the invention each of at least two of the plurality of capsules contains therein a different flavor material.

According to some embodiments of the invention each of at least two of the plurality of capsules contains the same flavor material but at a different concentration.

According to some embodiments of the invention the dispenser system comprises a plurality of dispensing elements and wherein the controller signals each dispensing element to dispense a fluid obtained from a flavor material contained in a different capsule.

According to some embodiments of the invention the dispenser system comprises at least one fluid channel forming fluid communication between a respective compartment and the environment, wherein the controller is configured for opening and blocking the at least one fluid channel, thereby to establish or prevent the fluid communication.

According to some embodiments of the invention the system comprises a mixing chamber, wherein the dispenser system comprises at least one fluid channel forming fluid communication between a respective compartment and the mixing chamber, and wherein the controller is configured for opening and blocking the at least one fluid channel, thereby to establish or prevent the fluid communication.

According to some embodiments of the invention the system comprises a weight measuring device constituted to measure a weight of each capsule separately.

According to some embodiments of the invention the user interface is configured for at least one of (i) activating the controller and/or the dispenser system, (ii) deactivating the controller and/or the dispenser system, and (iii) entering the selection data.

According to some embodiments of the invention the system comprises a weight measuring device constituted to measure a weight of each capsule separately, wherein the controller is configured for receiving weight data from the weight measuring device and to control the amounts based on the weight data.

According to some embodiments of the invention the system comprises a communication system configured for communicating with a remote user interface.

According to some embodiments of the invention the dispenser system is configured for heating the flavor material to form the fluid.

According to some embodiments of the invention the dispenser system is configured to apply ultrasound waves to the flavor material thereby to dispense the fluid.

According to some embodiments of the invention the dispenser system is configured to apply a stream of gas to the flavor material thereby to dispense the fluid.

According to some embodiments of the invention the dispenser system comprises an atomizer.

According to some embodiments of the invention the dispenser system comprises a humidifier.

According to some embodiments of the invention the dispenser system comprises a blower or a fan.

According to some embodiments of the invention at least one of the capsules contains the flavor material in a solid state as room temperature.

According to some embodiments of the invention at least one of the capsules contains the flavor material in a liquid state as room temperature.

According to some embodiments of the invention at least one of the capsules contains the flavor material in a gaseous state as room temperature.

According to some embodiments of the invention the flavor material in at least one of the capsules is a scent material.

According to an aspect of some embodiments of the present invention there is provided a method of releasing a flavor into an environment. The method comprises loading into the system as delineated hereinabove, and optionally and preferably as detailed below, a plurality of capsules, each containing therein a flavor material, and activating the system to dispense a fluid obtained from a flavor materials contained in at least one of the capsules.

According to some embodiments of the invention the method wherein the environment is selected from the group consisting of a living room, a bedroom, a kitchen, a lavatory, a hotel room, a lobby, a waiting room, an office, a restaurant, a massage parlor and a vehicle.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
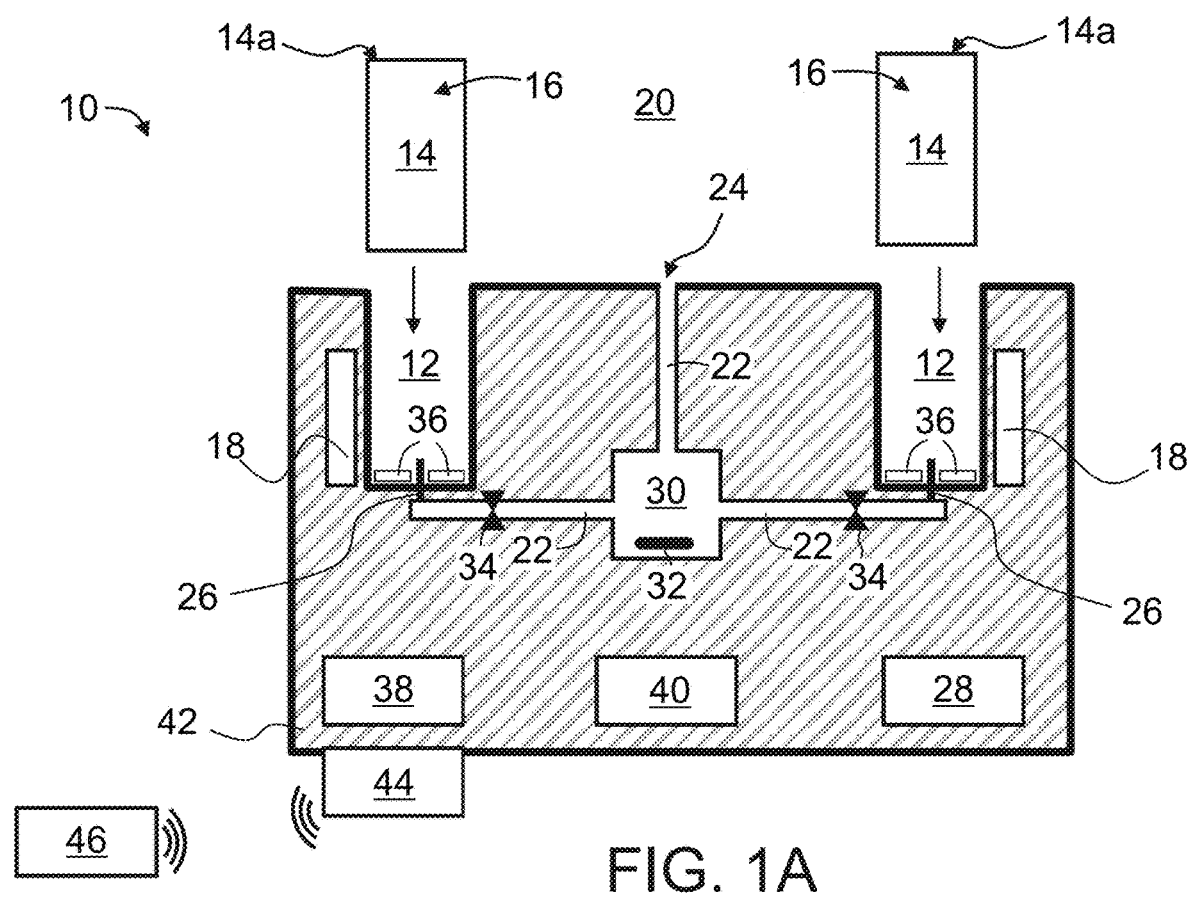
FIG. 1A is a schematic illustration of a system for releasing a flavor into the environment, according to some embodiments of the present invention.

The present invention, in some embodiments thereof, relates to the release of a fluid to the environment and, more particularly, but not exclusively, to a system and method for releasing flavor.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
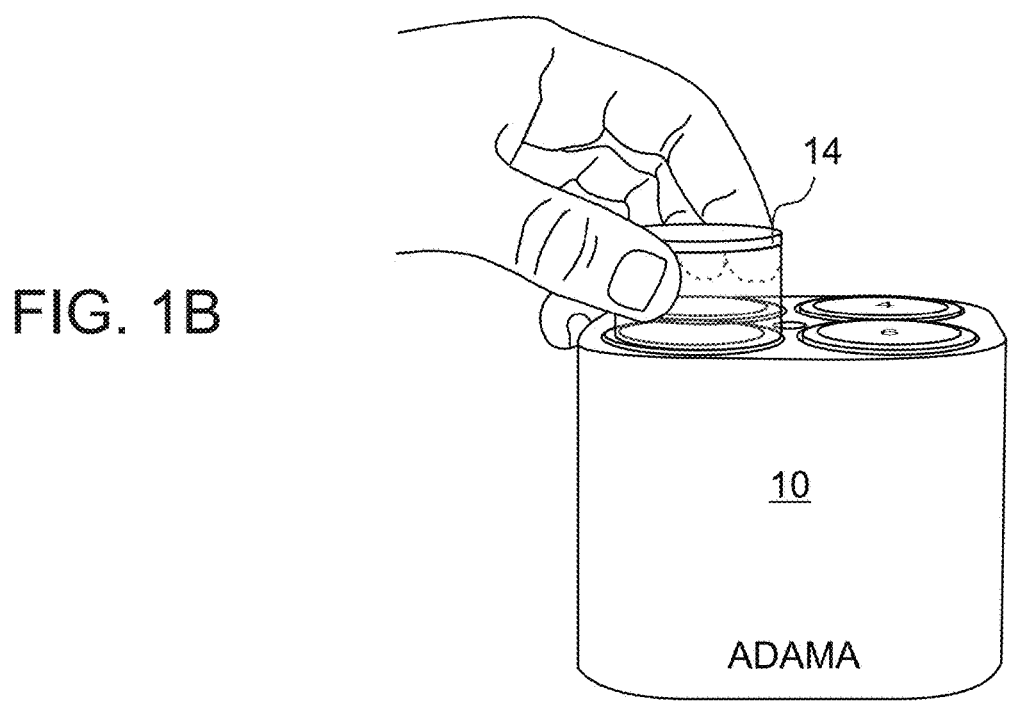
FIG. 1B is an image of a system for releasing a flavor into the environment, according to some embodiments of the present invention.

Referring now to the drawings, FIGS. 1A and 1B is a schematic illustration (FIG. 1A) and an image (FIG. 1B) of a system 10 for releasing a flavor into the environment, according to some embodiments of the present invention. System 10 is optionally and preferably electrically operated either by means of batteries and/or by connecting the system to a DC or AC power source.

System 10 preferably comprises one or more compartments 12, preferably a plurality of compartments 12. FIG. 1A shows two compartments and FIG. 1B shows four compartments, but system 10 can include an number of compartments, preferably four or more.

Each of the compartments is adapted to receive a capsule 14 containing therein a flavor material 16.

While FIGS. 1A and 1B show embodiments in which the capsules are received by the compartments from above, this need not necessarily be the case, since, for some applications, it may be desired to construct the compartments to receive the capsules from the side or from below. The present embodiments also contemplate configurations in which one or more compartments receive the capsules from above, and one or more compartments receive the capsules from the side.

The flavor material in the capsules is typically a scent material.

As used herein, "scent material" refers to any substance that comprises one or more odorant components.

As used herein, "odorant component" refers to a monomolecular substance which can be sensed by the olfactory receptors and is perceived as having a smell in humans. In some embodiments of the present invention odorant component is perceived as having a smell also in other life forms including, without limitation, animals, insects, spiders and the like.

The scent material of the present embodiments encompasses natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. A scent material may also include an auxiliary material, such as a fixative, an extender, a stabilizer and a solvent.

The scent material is typically pleasant but other scent materials are also contemplated, whether agreeable or offensive.

When the capsule contains a scent material, system 10 can be used to modify the odor in the environment. Representative examples of environments in which system 10 is useful including, without limitation, a living room, a bedroom, a kitchen, a lavatory, a hotel room, a lobby, a waiting room, an office, a restaurant, a massage parlor, a vehicle (e.g., a car), a theatre and the like.

The scent material can be any natural substance, synthetic material, (incorporating aldehydes, ketones, esters, and other chemical constituents), or combinations thereof which is known in the art and suitable for imparting an odor, aroma, or fragrance. Suitable natural and synthetic scent material include those compiled by the U.S. Food and Drug Administration in Title 21 of the Code of Federal Regulations, Sections 172.510 and 172.515 respectively and by IFRA. Suitable scent materials include spice oil, flower oil, and fruit oil. The scent material may contain fragrance components, for example benzaldehydes, phenols, cinnamic aldehydes and esters, octadienes, dienes, cyclohexadienes, terpenes and any aroma ingredient.

The scent material may, in some embodiments, comprise an essential oil in a carrier such as water and/or alcohol or other organic solvent or a perfume. The scent material may be that of a fruit and berry scents such as: citrus, almond, apple, cherry, grape, pear, pineapple, orange, strawberry, raspberry, and musk; flower scents such as lavender, rose, iris, carnation, gardenia, tea rose, violet, hyacinth, magnolia, mimosa, honeysuckle, jasmine, narcissus, orange blossom, orchids, sweet pea, tuberose, and lilac; forest and herbal smells such as evergreen cedar, pine, sassafras, and spruce; essential oils such as spice, peppermint, vanilla, spearmint; and various other fragrances such as leather, new car odor, acacia, cassie, cypre, cyclamen, fern, hawthorn and the like.

Representative examples of active ingredients that the scent material can comprise according to some embodiments of the present invention, include, without limitation, scent materials marketed by Agan Aroma, Israel, such as, but not limited to, 1,3,4,6,7,8-Hexahydro-4,6,6,7,8,8-hexamethyl-cyclopenta-2-benzopyran, 1,3,4,6,7,8-Hexahydro-4,6,6,7,8,8-hexamethyl-cyclopenta-2-benzopyran, 7-methyl-3,4-dihydro-2H1,5 benzodioxepin-3-one, 1,3,4,6,7,8-Hexahydro-4,6,6,7,8,8-hexamethyl-cyclopenta-2-benzopyran, 1,3,4,6,7,8-Hexahydro-4,6,6,7,8,8-hexamethyl-cyclopenta-2-benzopyran, 1,3,4,6,7,8-Hexahydro-4,6,6,7,8,8-hexamethyl-cyclopenta-2-benzopyran, cis-3-hexenyl acetate, a-Methyl-3,4-methylendioxy hydrocinnamaldehyde, cis-3-Hexen-1-ol, Benzoic acid, 2-hydroxy-, 3-hexenyl ester, (Z)-, 2 Acetonaphtone-1,2,3,4,5,6,7,8-octahydro-2,3,8,8-tetramethyl, 7-acetyl-1,1,3,4,4,6 hexamethyltetraline, Methyl1-2,4-dihydroxy-3,6-dimethyl-benzoate, 1-2,6,6-trimethy-3-cyclohexen-1-yl-2-buten-1-one, e,e-8,10-dodecadien-1-ol, and (z)-11-tetradecenyl acetate.

Additional example of ingredients that the scent material can comprise according to some embodiments of the present invention, include, without limitation, allyl heptanoate, anethole USP, benzaldehyde, benzyl acetate, cis-3-hexenyl acetate, cis-jasmone, coumarin, dihydromyrcenol, dimethyl benzyl carbinyl acetate, ethyl vanillin, eucalyptol, eugenol, iso eugenol, isobutyl salicylate, flor acetate, geraniol, hydroxycitronellal, koavone, dihydro linalool, linalool, methyl anthranilate, methyl beta naphthyl ketone, methyl dihydro jasmonate, nerol, nonalactone, orange flower ether, phenyl ethyl acetate, phenyl ethyl alcohol, phenyl propyl alcohol, phenoxy ethyl isobutyrate, phenoxanol, alpha terpineol, tetrahydro linalool, beta terpineol, vanillin, and mixtures thereof.

The scent material can, in some embodiments, comprise one or more substances having a CAS No. selected from the group consisting of the CAS Nos. listed in Appendix A.

The flavor material can be in a solid state or in a liquid state or in a gaseous state at room temperature. Typically, the flavor material is in a liquid state at room temperature.

In some embodiments, two or more of the capsules, optionally and preferably all the capsules, contain different flavor materials, in some embodiments two or more of the capsules contain the same flavor material, and in some embodiments two or more of the capsules contain same flavor material but at a different concentration.

In some embodiments of the present invention system 10 comprises a dispenser system 18 configured for dispensing into the environment 20 a fluid obtained from at least one flavor material in the capsules. Dispenser system 18 is shown in FIG. 1A as separate dispensing elements, one for each compartment, but this need not necessarily be the case, since, for some applications, system 18 can be provided, for example, as a single unit.

Dispenser system 18 can employ any technology that allows obtaining a fluid from the flavor material in the capsules.

In some embodiments of the present invention system 18 employs heating. In these embodiments, the heat provides the flavor material with thermal energy that breaks up or excites the bonds of flavor molecules (e.g., odorant components, or taste modifiers) and allows them to flow. The heat can be applied by convection, radiation or conduction. In some embodiments of the present invention system 18 comprises a heat source, e.g., a flame based heat source, or, more preferably, a resistive heat source, e.g., in the form of a filament resistor, a power resistor or a coil. In some embodiments of the present invention system 18 comprises a light source that directs radiation onto the flavor material at a wavelength that heats the material. For example, the light source can apply infrared radiation.

In some embodiments of the present invention system 18 applies ultrasound waves to the flavor material. The ultrasound wave provides the flavor material with mechanical energy (e.g., vibration) that breaks up or excites the bonds of flavor molecules (e.g., odorant components, or taste modifiers) and allows them to flow.

In some embodiments of the present invention system 18 atomizes the flavor material.

As used herein "atomizing" and "atomization" refer to the conversion of a liquid medium into a spray or mist (i.e., a collection of droplets). Atomization can occur by passing a liquid medium through a nozzle or aperture. The terms "atomizing" and "atomization" do not necessarily mean that the spray or mist or the particles therefrom are reduced to atomic sizes. Atomizing a liquid medium can be achieved by use of an atomizer. Atomizers are known and are commercially available, such as from TSI, Inc. of Shoreview Minn., USA.

In some embodiments of the present invention system 18 humidifies the air nearby the flavor material.

The term "humidifying" and "humidification" refer to the process of adding moisture to a gas.

Humidification can be achieved by a humidifier. Humidifiers are known per se and can be of a warm air type or a cold air type. A warm air type humidifier use either a vaporizer or warm mist generator to heat the flavor material and add flavor moisture to the air. A cool air type humidifier generates moisture mechanically, for example, by means of a fan, a blower, a spinning disk or an ultrasonic wave.

System 18 can also generate gas flow (e.g., airflow) that moves fluid obtained from the flavor material away from the capsules. This can be done by a fan or a blower, as known in the art. Generation of gas flow by fan or a blower can be a supplement by one or more of the above technique. Alternatively, system 18 can employ a fan or a blower without heating, without atomizing and without applying ultrasound wave, for example, according to the principle of cool air type humidification.

System 18 can release the fluid directly into the environment, for example, through an upper surface 14a of capsule 14. In these embodiments, upper surface 14a is preferably exposed to the environment and is made permeable to the fluid that is formed from the flavor material, but not to the flavor material itself. These embodiments are useful when the flavor material is in solid form or when the molecules of the obtained fluid are substantially smaller than the molecules of the flavor material.

Alternatively, system 18 can comprise one or more fluid channel 22 into which the fluid is released. One or more of the fluid channels can have an opening 24 to the environment 20, so that fluid obtained from the flavor material in a particular capsule, or fluids obtained from flavor materials in several capsules can be released through opening 24.

In some embodiments of the present invention compartment 12 includes a piercing member 26 (such a nozzle or a hollow needle) that pierces the capsule and establishes fluid communication with fluid channel 22. Piercing member 26 can be positioned to protrude inwardly from the base of compartment 12, as illustrated in FIG. 1A. Alternatively, piercing member 26 can protrude inwardly from the side walls of compartment 12. When the compartment receives the capsule not from above, the piercing member can protrude inwardly from a top surface (not shown) of the compartment. Also contemplated are embodiments in which several piercing members are employed, for example, one or more at the base of the compartment and/or one or more at the side walls of the compartment.

The piercing member can be static in which case the capsule is pierced once fitted into the respective compartment. For example, when a static piercing member protrudes outwardly from the base of the comportment, the operator can conveniently press on the upper surface 14a of the capsule to effect the piercing. The piercing member can alternatively be movable perpendicularly to the inner surface (base, side wall, upper surface) of the compartment from which the piercing is effected. Piercing of the capsule is effected when the piercing member moves inwardly. Once the capsule is pierced, the piercing member can be retracted backwardly. Inward and backward motion of the piercing member can be established by a controller as further detailed hereinbelow, or manually, for example, by means of a lever or a button (not shown).

Once the capsule is pierced, fluid obtained from the flavor material flows through the thus formed piercing from the capsule into the channel 22 and then from channel 22 into the environment 20. Alternatively, the fluid can flow from the capsules into a mixing chamber 30 and then from the mixing chamber into the environment. The flow from the mixing chamber 30 to the environment can be achieved by virtue of an increased gas pressure in chamber 30 relative to the environment, or by means of a fan or a blower 32 operated by dispenser system 18.

In various exemplary embodiments of the invention system 10 comprises a controller 28 configured for automatically selecting a dispensing protocol, and for signaling dispenser system 18 to dispense fluids obtained from one or more flavor materials contained in one or more capsules of the compartments.

The dispensing protocol optionally and preferably includes one or, more preferably, a set of parameters that characterize the dispensing process. For example, the dispensing protocol can include one or more parameters pertaining to a mixing ratio between two or more fluids dispensed from respective two or more flavor materials in respective two or more capsules. The dispensing protocol can include one or more parameters pertaining to an amount of dispensed fluid in each dispensing activity. The dispensing protocol can include one or more parameters pertaining to an identification of one or more compartments that hold capsules from which one or more fluids are dispensed. The dispensing protocol can include one or more parameters pertaining to dispensing timing, including, without limitation, intervals between dispensing events, duration of each dispensing event and/or time of the day in which the dispensing occurs.

In various exemplary embodiments of the invention controller 28 automatically re-executes the dispensing protocol selection and the signaling. Preferably, the re-execution is according to a shuffle protocol. For example, controller 28 can select a compartment, signals dispenser system 18 to dispense the fluid obtained from flavor material contained in the capsule of the selected compartment for a predetermined time-duration, and then selects another compartment and signals dispenser system 18 to dispense the fluids obtained from flavor materials contained in the capsule of the newly selected compartment, for the same or different time-duration and so on. In another example, controller 28 can select a first mixing ratio between two or more fluids from respective two or more flavor materials contained in respective two or more capsules, signals dispenser system 18 to dispense the respective fluids according to the selected mixing ratio, selects another mixing ratio, and signals dispenser system 18 to dispense the respective fluids according to the newly elected mixing ratio and so on.

The shuffle protocol applied by controller 28 can includes probabilities for selecting compartment, probabilities for selecting mixing ratios, probabilities for selecting amounts of dispensed fluids, probabilities for selecting time-durations for dispensing the fluids, and/or probabilities for selecting time intervals between successive selections (which are typically, but not necessarily, the same as time-durations for dispensing the fluids). Alternatively, and more preferably, controller 28 can select a dispensing protocol from a list of several dispensing protocols (each characterized by one or more parameters, as further detailed hereinabove), in which case it is sufficient for the shuffle protocol to include probabilities for selecting the dispensing protocols.

The selection can be random according to a predetermined statistical distribution. The statistical distribution can be of any type. In some embodiments of the present invention a uniform statistical distribution, in which case all dispensing protocols have equal probabilities to be selected. In some embodiments of the present invention a biased statistical distribution is employed, wherein some dispensing protocols have higher probabilities to be selected than other dispensing protocols. This can be achieved, for example, by assigned with different weight values to two or more dispensing protocols, so that dispensing protocols with higher weight values have higher probabilities to be selected than dispensing protocols with lower weight values. The biasing can be according to a predetermined criterion or set of criteria. For example, the flavor materials can be categorized into categories (e.g., floral flavors, woody flavors, fresh flavors, oriental flavors, etc.) and the criterion or set of criteria can be that one or more categories are prioritized over other categories, wherein the prioritizing is effected by ensuring that the probabilities for selecting members of the prioritized categories are higher than the probabilities for selecting members of non-prioritized categories.

The shuffling protocol can alternatively or additionally be applied to vary one or more parameters individually. For example, controller 28 can execute shuffling between the compartment from which the fluids are dispensed, and/or shuffling between dispensing activities with a higher dispensing rate and dispensing activities with a lower dispensing rate, and/or shuffling between dispensing activities with a higher duration and dispensing activities with a lower duration, and/or shuffling between dispensing activities with longer pauses between dispensing events and dispensing activities with shorter pauses between dispensing events, etc.

In some embodiments of the present invention controller 28 is configured to extract information pertaining to contents of the capsules in the containers. The information can be extracted, for example, by providing the capsules with an identification tag as further detailed hereinbelow.

The extracted information can include, for example, the type of flavor and/or the flavor category or categories in which the corresponding flavor is a member, the strength of the scent produced by the flavor (e.g., scaled according to the Weber-Fechner law), etc. The extracted information can be used by controller 28 to select the dispensing protocol, for example, by biasing the probabilities to select the dispensing protocols according to the compartments employed by these dispensing protocols, and based on the extracted information, e.g., using a biased statistical distribution as further detailed hereinabove. The extracted information can alternatively or additionally be used for automatically select a shuffle protocol.

For example, controller 28 can access a computer readable medium storing a collection of shuffle protocols and select a shuffle protocol for execution based on information. For example, when the extracted information indicates that the capsules that are currently loaded to system 10 contain flavors of particular categories, controller 28 can select a shuffle protocol that is particularly adapted for these categories.

Controller 28 can cause the release of fluids obtained from two or more capsules simultaneously. This can be achieved by simultaneous activation of different dispensing elements, or by allowing fluids to mix at mixing chamber prior to their release.

There are several advantages for the ability to release more than one fluid. For example, in order to control odors already present in the environment, one selected compartment can contain a capsule having a fragrance and another compartment can contain a capsule having an odor neutralizing material. Depending on the fragrance and the odor neutralizing material can be selected. Another advantage is that selecting more than one compartment can allow the operator to cause system 10 to release flavor combinations according to the desire of the user. A further advantage is that selecting more than one compartment can increase significantly the variety and spectrum of flavors that can be dispensed by system 10.

When dispenser system 18 comprises a plurality of dispensing elements, controller 28 optionally and preferably signals each of the dispensing elements independently.

When system 10 comprises mixing chamber 30, controller 28 optionally and preferably opens, at least temporarily, fluid channels from the selected compartments to mixing chamber 30. This can be achieved by providing one or more of channels 22 with valves 34 that are controlled by controller 28. Also contemplated are embodiments in which the flow of scent material out of each individual capsule 14 into the respective channels 22 is by a fan or a blower that is controlled independently by controller 28. In these embodiments, the mixing ratio between the scents in the respective capsules can be set by controlling the rotation speed of the respective fans.

When system 10 comprises movable piercing members 26, controller 28 can also control the operation of piercing members 26. For example, during the loading of a capsule into one of the compartments, the piercing member can be in a backward state (namely not protruding inwardly with respect to the interior of the compartment).

Once the data pertaining to the selection of two or more compartments is received by controller 28 and system 10 is in operation, controller 28 can signal only the piercing members of the selected compartment to pierce the respective capsule, thereby ensuring that only fluids that are obtained from the capsules in the selected compartments are eventually released into the environment.

Alternatively, all the capsules can be pierced and the control over the release of a particular fluid to the environment can be achieved by means of controlling valves 34 and/or whether or not the respective dispensing element is operative.

In some embodiments of the present invention controller 28 also receives data pertaining to a mixing ratio, and controls the amounts of fluids obtained from different flavor materials responsively to the received mixing ratio. Controller 28 can optionally and preferably apply shuffling to the mixing ratio itself. This is preferably done by shuffling among several fixed mixing ratios. Alternatively, the mixing ratio shuffling can be achieved by independently varying the amounts of fluids obtained from different flavor materials.

The control over the amount of a particular fluid that is eventually released into the environment (either directly or via fluid channel 22 or via mixing chamber 30) can be achieved in more than one way.

For example, in some embodiments of the present invention by a timing protocol is executed, wherein the time during which a particular fluid is allowed to flow is selected based on the mixing ratio. For example, when it is desired to mix a flavor from a first capsule and a flavor from a second capsule at a ratio of 2:1, the fluid from the first capsule can be allowed to flow during a certain time interval Δt and the fluid from the second capsule can be allowed to flow during half the interval Δt. Thus, in these embodiments, controller 28 can apply the mixing ratio shuffling by varying the timing protocol.

In embodiments of the present invention in which the flow of scent material out of each individual capsule 14 into the respective channels 22 is by a fan or a blower that is controlled independently by controller 28, the mixing ratio between the scents in the respective capsules can be set by controlling the rotation speed of the respective fans. For example, when it is desired to mix a flavor from a first capsule and a flavor from a second capsule at a ratio of 2:1, the fan or blower that generates flow out of the first capsule can rotate at a rotation speed that is higher (e.g., two times higher) than the rotation speed of the fan or blower that generates flow out of the second capsule. Thus, in these embodiments, controller 28 can apply the mixing ratio shuffling by varying the rotation speeds of the fans.

In some embodiments of the present invention system 10 comprises a weight measuring device 36 constituted to measure a weight of each capsule separately. This embodiment is useful for determining the amount of flavor material that remains in each capsule, for example, for the purpose of providing notification to the operator.

Optionally, system 10 comprises a display 38, and controller 28 receives weight data from device 36 and controls display 38 to present information to the operator. Information may include information pertinent to battery life, duration or other suitable indicator associated with capsule replacement, mixing ratio, scent intensity and the like. It is appreciated that the list of information provided above is not exhaustive but, rather is representative of various parameters that a user may find valuable in assessing and/or maintaining a desired operation of system 10. Display 38 may be an LCD or a LED display or other suitable display capable of displaying one or more parameters associated with the operation of the device.

The weight data can also be used by controller 28 for maintaining the mixing ration between fluids. Based on the change in the weight of each capsule, the controller can predetermine the amount of the fluid that has been obtained from the respective capsule, and can therefore control the flow of the respective fluids so as to maintain the ratio.

System 10 preferably comprises a user interface 40. The user interface may include buttons, which are activated by pressing, and may take different shapes depending on each button's particular function. The user interface may also include LEDs to indicate operational status information such as low battery or low level of flavor material in a particular capsule. The user interface may also include a touch screen or a keyboard. The user interface may also be a voice activated interface.

The user interface can allow the operator to program the release of fluids in a manner preferred by the operator. For example, the user interface may allow the user to program the speed of dispensing, e.g., by choosing the number of days of dispensing, the amount of each dispense activity, the hours of the day associated with dispensing, the duration of the dispensing, etc. It is understood that selecting a shorter duration at a greater rate of dispensing and selecting longer duration at a slower rate of dispensing can generate similar scent duration and intensity profiles.

The user interface can also allow the user to program other features of system 10 such as, but not limited to, daylight settings, on and off hours, and the like. In various exemplary embodiments of the invention the user interface allows the operator to activate and/or deactivate system 10 or any component thereof separately (dispenser system 18, controller 28), to enter selection data indicating which of the capsules will be active, and/or to enter the mixing ratio. User interface 40 can be mounted on an encapsulation 42 of system 10.

The user interface 40 can also allow the operator to select between a mode of operation is which a shuffle protocol is employed, and a mode of operation in which dispensing is executed without shuffling. The user interface 40 can allow the operator to select the shuffle protocol. For example, user interface 40 can present the operator with a list (e.g., a dropdown menu) of available shuffle protocols, and controller 28 can apply the shuffle protocol selected by the operator. The user interface 40 can additionally or alternatively allow the operator to select a parameter or parameters for the shuffle protocol. Such a parameter or parameters may include, but are not limited to, compartment selection probabilities, mixing ratio selection probabilities, time-durations for dispensing the fluids, time intervals between successive selections, and the like.

In some embodiments, system 10 is remotely activated. In these embodiments, system 10 comprises a communication system 44 configured for communicating with a remote user interface 46. For example, user interface 46 can be a smart home control system, and controller 28 can transmit to the smart home control system, via communication system 44, signals pertaining to the state of system 10 and to receive from the smart home control system control signals than can include activation and/or deactivation signals, signals carrying selection data, signals carrying mixing ratio, and the like. The communication between interface 46 and communication system 44 can be via near field wireless communication technology.

Correspondingly, interface 46 can be selected from a group consisting of a mobile phone, a tablet computer, and a notebook computer, which is provided with BLUETOOTH, Z-wave, ZigBee, or WIFI communication functions. The communication can also be via Internet, GPRS, GSM, CDMA, 3G, or 4 G communication technologies. Correspondingly, interface 46 can be a computer, which can be connected to Internet, or may be a mobile phone, which is provided with GPRS, GSM, CDMA, 3G, or 4G communication functions. The communication may empower the user to combine the scent with other solutions which impact or optimize the ambiance at the home or office or other place of operation. Other such ambiance effectors may be systems which modify the temperature, music or noise, alarm system, humidity, lighting and so on.

Figure 2:
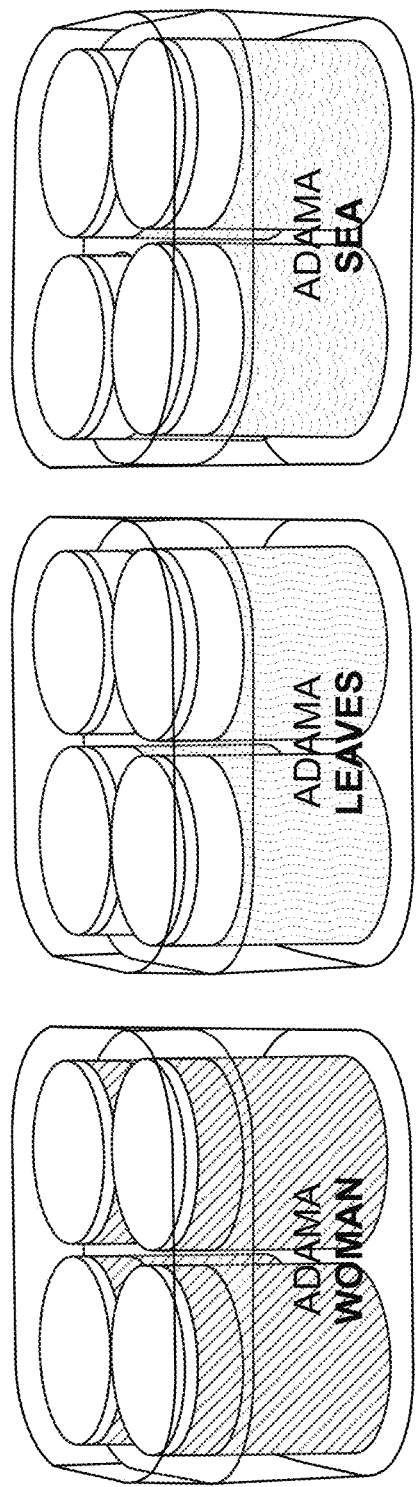
FIG. 2 is an image showing representative example of packages of flavor capsules, according to some embodiments of the present invention.

System 10 can provide sensible scent to any environment, typically, but not necessarily, having an area of from about 4 square meters to about 25 square meters and a height of from about 2 meters to about 5 meters. The duration of operation of each capsule is optionally and preferably from about 2 hours to about 24 hours. The capsules are preferably for a single use. The volume of flavor material in each capsule can be from about 2 ml to about 10 ml. Other sizes and durations are not excluded from the scope of the present invention. The capsules can be provided to the consumer separately from system 10. For example, packages of several capsules can be marketed, wherein each package can include capsules containing the same or different flavor material. FIG. 2 is an image showing representative example of such packaging, wherein each package includes four capsules of the same flavor. Other packaging forms are also contemplated.

Figure 3A:
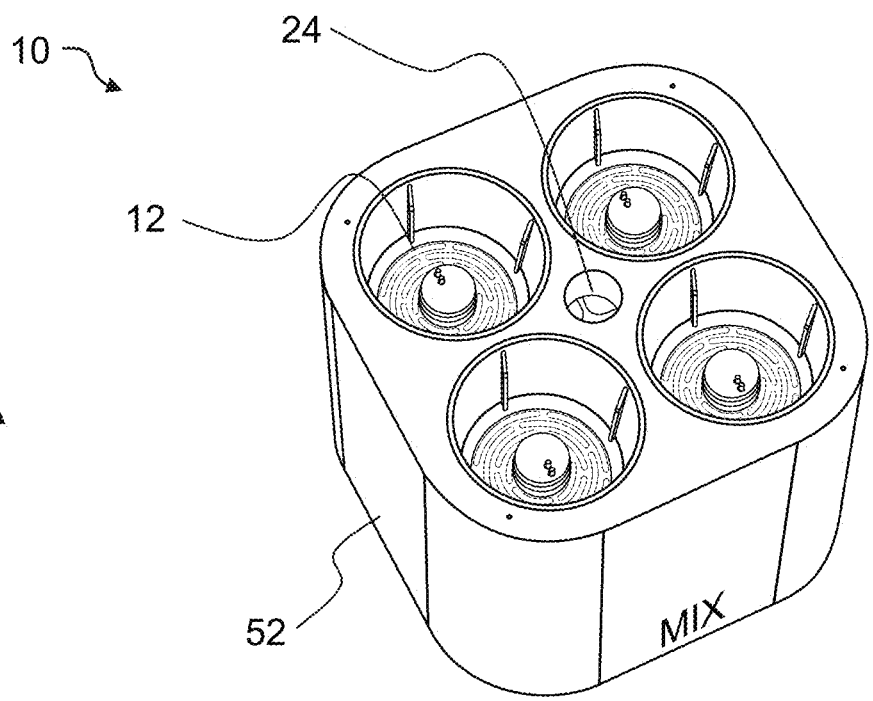
FIGS. 3A-H are schematic illustrations of the system in embodiments of the invention in which the gas flows from a plurality of capsules by means of a respective plurality of individual fans.
Figure 3B:
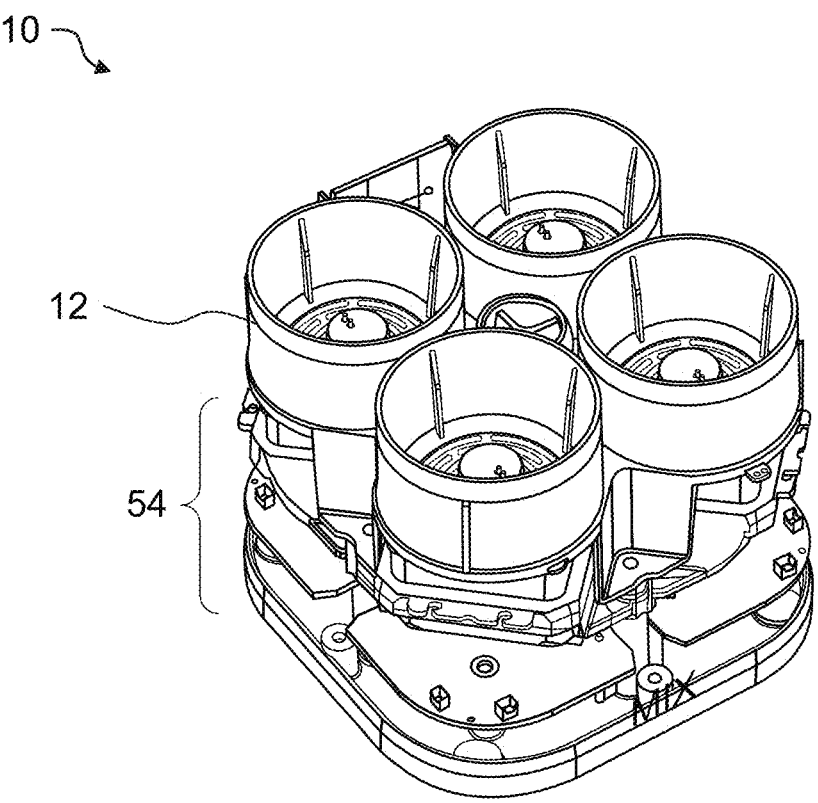

Reference is now made to FIGS. 3A-H which are schematic illustrations of system 10 in embodiments of the invention in which the gas flows downwards from the capsules. FIG. 3A is a perspective view of system 10 showing compartments 12, opening 24 and a casing 52 enclosing the various components of system 10. FIG. 3B is a perspective view of system 10 without the casing 52, showing the compartments 12 connected to a base assembly 54 which is better illustrated in FIGS. 3G and 3H described below.

Figure 3C:
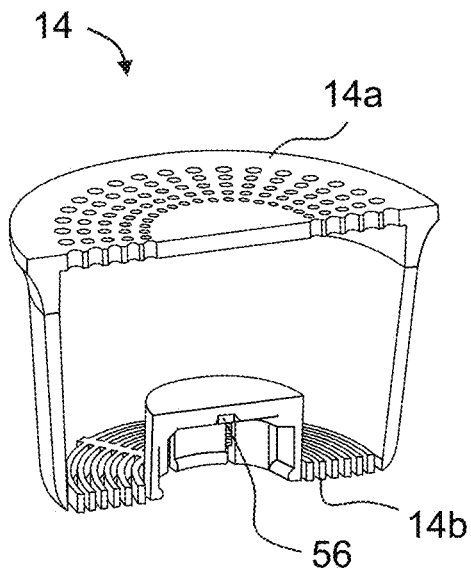
Figure 3D:
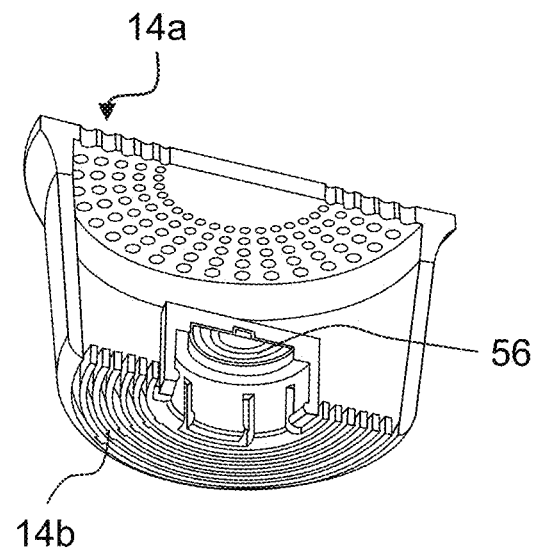

FIGS. 3C and 3D illustrate two different perspective views of capsules 14 made size-wise and shape-wise compatible with the compartment 12. The capsules 14 are formed with an entry grid at their upper surface 14a and an exit grid at their bottom surface 14b. In operation, air from the environment enters the capsules 14 through the grid at the upper surface 14a and scent material exits the capsules 14 through the grid at the bottom surface 14b.

Figure 3E:
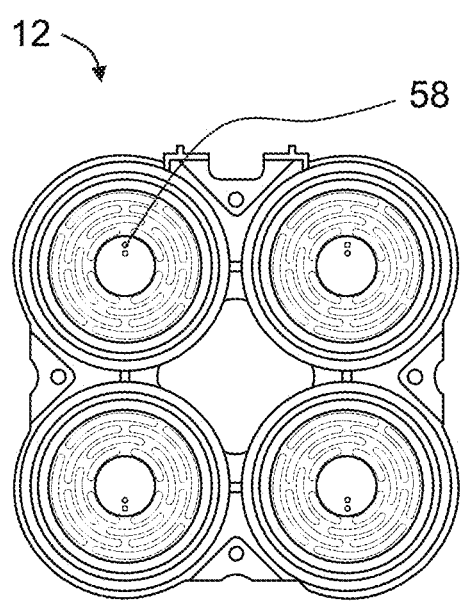
Figure 3F:
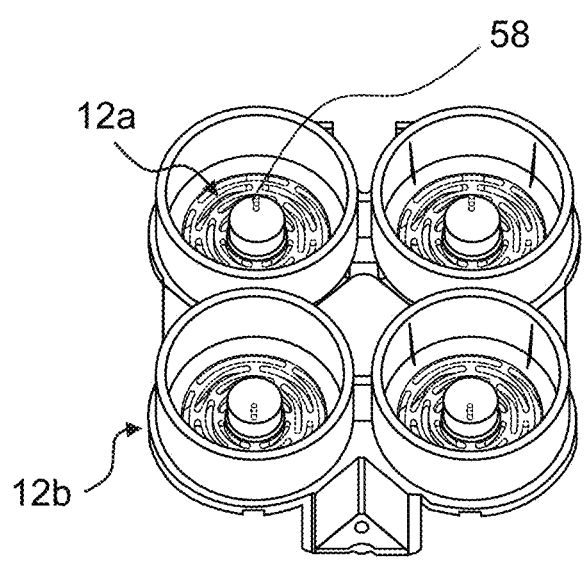

FIGS. 3E and 3F illustrate a top view (FIG. 3E) and a perspective view (FIG. 3F) of compartments 12. In these embodiments, compartments 12 are open at their upper side 12a so as to allow compartments 12 to receive capsules 14, and have a grid at their bottom side 12b. In operation, the scent material exiting the capsules 14 through the grid at the bottom surface 14b passes through the grid as the bottom side 12b of compartments 12.

In some embodiments of the present invention capsules 14 comprise an identification tag 56. Identification tag 56 provides identification pertaining to at least one property of capsule, including, without limitation, the authenticity of the capsule, the type and/or concentration of the scent material in the capsules, the amount of scent material in the capsules, the elapsed time during which the capsule was operative, etc. Identification tag 56 can be of any machine-readable type known in the art, such as, but not limited to, a barcode (e.g. a QR tag), an RFID and an RTLS.

In embodiments in which capsules 14 comprise an identification tag, one or more of compartments 12 optionally comprises a tag reading circuit 58 that is configured for reading the data from the identification tag. The data obtained by tag reading circuit 58 can optionally and preferably transmitted to controller 28 which can operate system 10 based on the data. For example, when the data indicate that the capsule is not authentic, the controller can stop the operation of system 10, and when the data include the type of scent material, the controller can operate system 10 based on the selected protocol and on the identified type of scent material.

Figure 3G:
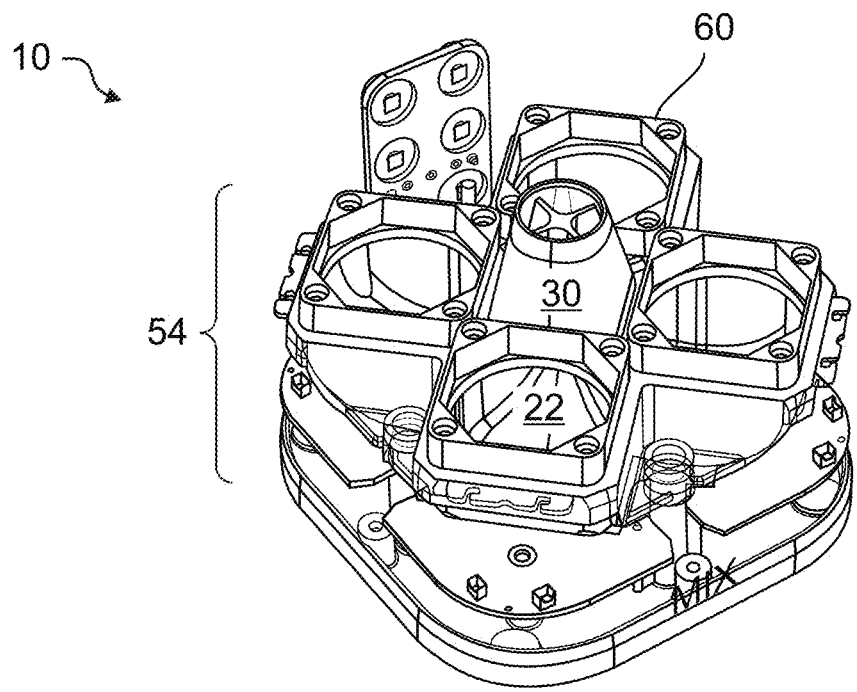
Figure 3H:
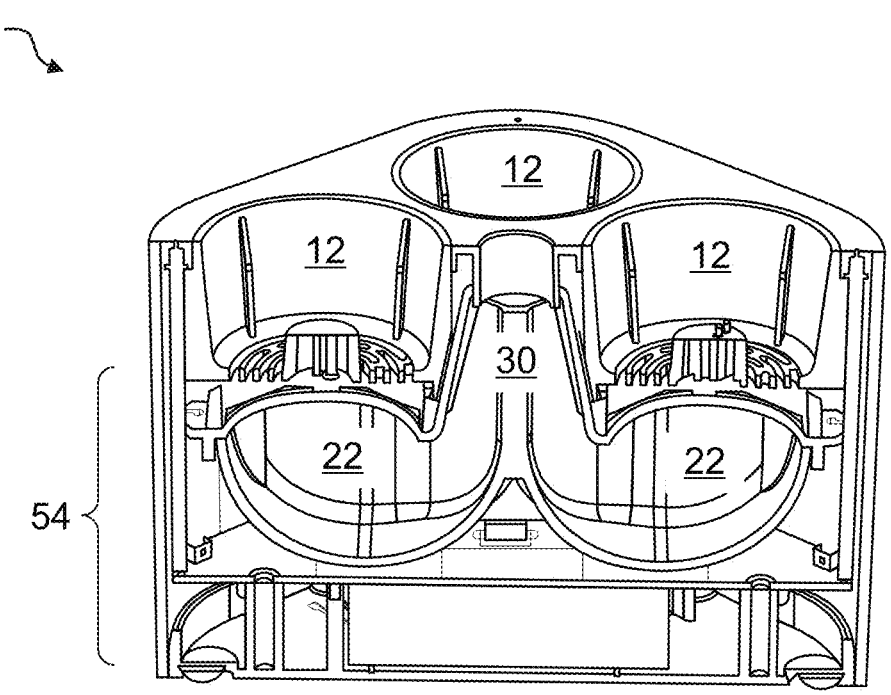

FIGS. 3G and 3H illustrate a perspective view (FIG. 3G) and a cross sectional view (FIG. 3H) of base assembly 54, according to some embodiments of the present invention. Base assembly comprises one or more fans or blowers fitted into holding frames 60. For clarity of presentation, the fans themselves are not illustrated in FIG. 3G. Base assembly 54 also comprises fluid channels 22 each positioned at the outlet of a respective fan. The fans or blowers are mounted on holding frames 60 to rotate in a direction that generates flow of scent material out of the grid at the bottom 14b of the capsules, through the grid at the bottom 12b of the compartments and into the fluid channels 22. The scent from the individual compartments 12 is guided by channels 22 into an exit fluid channel serving as mixing chamber 30. In the representative illustration of FIGS. 3G and 3H, the exit fluid channel 30 has a tapered shape (for example, a conical shape) but this need not necessarily be the case since the exit fluid channel 30 can have a non-tapered shape. From the exit fluid channel 30, the mixed scent exits system 10 via opening 24.

Appendix A

The scent material can, in some embodiments, comprise one or more substances having a CAS No. selected from the group consisting of 56-81-5, 59-02-9, 60-12-8, 60-33-3, 60-33-3, 64-17-5, 66-25-1, 71-23-8, 71-36-3, 71-41-0, 74-93-1, 75-18-3, 75-65-0, 76-09-5, 76-22-2, 76-49-3, 76-50-6, 77-42-9, 77-52-1, 77-53-2, 77-54-3, 77-70-3, 77-83-8, 77-90-7, 78-35-3, 78-36-4, 78-37-5, 78-69-3, 78-70-6, 78-84-2, 78-92-2, 79-20-9, 79-31-2, 79-42-5, 79-69-6, 79-70-9, 79-76-5, 79-77-6, 79-78-7, 79-89-0, 79-92-5, 80-25-1, 80-26-2, 80-27-3, 80-54-6, 80-56-8, 80-57-9, 80-59-1, 80-71-7, 81-14-1, 83-34-1, 84-66-2, 85-91-6, 86-26-0, 87-19-4, 87-20-7, 87-22-9, 87-25-2, 87-41-2, 87-44-5, 87-55-8, 87-91-2, 88-09-5, 88-15-3, 88-40-4, 88-41-5, 88-60-8, 88-69-7, 88-84-6, 89-43-0, 89-48-5, 89-65-6, 89-71-4, 89-74-7, 89-78-1, 89-79-2, 89-80-5, 89-81-6, 89-82-7, 89-83-8, 89-88-3, 90-00-6, 90-02-8, 90-05-1, 90-12-0, 90-17-5, 90-42-6, 90-43-7, 90-87-9, 91-01-0, 91-10-1, 91-16-7, 91-20-3, 91-50-9, 91-51-0, 91-57-6, 91-61-2, 91-62-3, 91-63-4, 91-64-5, 91-87-2, 92-68-2, 93-04-9, 93-08-3, 93-15-2, 93-16-3, 93-18-5, 93-19-6, 93-28-7, 93-29-8, 93-51-6, 93-53-8, 93-54-9, 93-55-0, 93-58-3, 93-60-7, 93-89-0, 93-91-4, 93-92-5, 94-02-0, 94-08-6, 94-26-8, 94-30-4, 94-46-2, 94-47-3, 94-48-4, 94-50-8, 94-62-2, 94-86-0, 95-13-6, 95-16-9, 95-21-6, 95-41-0, 95-65-8, 95-87-4, 95-92-1, 96-04-8, 96-17-3, 96-22-0, 96-48-0, 97-41-6, 97-42-7, 97-45-0, 97-53-0, 97-54-1, 97-61-0, 97-62-1, 97-64-3, 97-85-8, 97-87-0, 97-89-2, 97-95-0, 97-99-4, 98-01-1, 98-02-2, 98-51-1, 98-52-2, 98-53-3, 98-55-5, 98-85-1, 98-86-2, 98-89-5, 99-48-9, 99-49-0, 99-72-9, 99-75-2, 99-83-2, 99-85-4, 99-86-5, 99-87-6, 99-89-8, 100-06-1, 100-41-4, 100-47-0, 100-51-6, 100-52-7, 100-66-3, 100-86-7, 101-39-3, 101-41-7, 101-48-4, 101-49-5, 101-81-5, 101-84-8, 101-85-9, 101-86-0, 101-86-0, 101-94-0, 101-97-3, 102-04-5, 102-13-6, 102-16-9, 102-17-0, 102-19-2, 102-20-5, 102-22-7, 103-05-9, 103-07-1, 103-09-3, 103-13-9, 103-23-1, 103-25-3, 103-26-4, 103-28-6, 103-29-7, 103-36-6, 103-37-7, 103-38-8, 103-41-3, 103-45-7, 103-48-0, 103-50-4, 103-52-6, 103-53-7, 103-54-8, 103-56-0, 103-58-2, 103-59-3, 103-60-6, 103-61-7, 103-82-2, 103-93-5, 103-95-7, 104-09-6, 104-20-1, 104-21-2, 104-45-0, 104-46-1, 104-50-7, 104-53-0, 104-54-1, 104-55-2, 104-57-4, 104-61-0, 104-62-1, 104-64-3, 104-65-4, 104-67-6, 104-76-7, 104-87-0, 104-93-8, 105-01-1, 105-13-5, 105-21-5, 105-37-3, 105-45-3, 105-53-3, 105-54-4, 105-57-7, 105-66-8, 105-67-9, 105-68-0, 105-70-4, 105-79-3, 105-82-8, 105-85-1, 105-86-2, 105-87-3, 105-89-5, 105-90-8, 105-91-9, 105-95-3, 106-02-5, 106-18-3, 106-21-8, 106-22-9, 106-23-0, 106-24-1, 106-25-2, 106-26-3, 106-27-4, 106-28-5, 106-29-6, 106-30-9, 106-32-1, 106-33-2, 106-35-4, 106-36-5, 106-44-5, 106-65-0, 106-68-3, 106-70-7, 106-72-9, 106-73-0, 106-79-6, 107-03-9, 107-54-0, 107-74-4, 107-75-5, 107-86-8, 107-87-9, 107-92-6, 107-98-2, 108-10-1, 108-11-2, 108-22-5, 108-29-2, 108-47-4, 108-48-5, 108-50-9, 108-64-5, 108-67-8, 108-68-9, 108-82-7, 108-83-8, 108-84-9, 108-93-0, 109-08-0, 109-15-9, 109-19-3, 109-20-6, 109-21-7, 109-25-1, 109-29-5, 109-29-5, 109-42-2, 109-43-3, 109-49-9, 109-52-4, 109-60-4, 109-94-4, 110-13-4, 110-19-0, 110-34-9, 110-36-1, 110-38-3, 110-39-4, 110-40-7, 110-41-8, 110-42-9, 110-43-0, 110-45-2, 110-62-3, 110-74-7, 110-89-4, 110-93-0, 110-98-5, 111-06-8, 111-11-5, 111-12-6, 111-13-7, 111-14-8, 111-27-3, 111-28-4, 111-30-8, 111-61-5, 111-62-6, 111-70-6, 111-71-7, 111-77-3, 111-79-5, 111-80-8, 111-81-9, 111-82-0, 111-84-2, 111-87-5, 112-05-0, 112-06-1, 112-12-9, 112-14-1, 112-17-4, 112-19-6, 112-23-2, 112-30-1, 112-31-2, 112-32-3, 112-37-8, 112-38-9, 112-39-0, 112-40-3, 112-42-5, 112-43-6, 112-44-7, 112-45-8, 112-45-8, 112-53-8, 112-54-9, 112-61-8, 112-62-9, 112-63-0, 112-66-3, 112-70-9, 112-72-1, 112-95-8, 115-18-4, 115-71-9, 115-95-7, 115-99-1, 116-02-9, 116-26-7, 116-53-0, 117-98-6, 118-58-1, 118-60-5, 118-61-6, 118-71-8, 118-93-4, 119-36-8, 119-53-9, 119-61-9, 120-11-6, 120-14-9, 120-24-1, 120-45-6, 120-50-3, 120-51-4, 120-57-0, 120-72-9, 120-92-3, 120-93-4, 121-32-4, 121-33-5, 121-34-6, 121-39-1, 121-97-1, 121-98-2, 122-00-9, 122-03-2, 122-27-0, 122-40-7, 122-43-0, 122-44-1, 122-45-2, 122-46-3, 122-48-5, 122-62-3, 122-63-4, 122-67-8, 122-68-9, 122-69-0, 122-70-3, 122-71-4, 122-72-5, 122-73-6, 122-74-7, 122-78-1, 122-78-1, 122-84-9, 122-91-8, 122-97-4, 122-99-6, 123-05-7, 123-07-9, 123-08-0, 123-11-5, 123-15-9, 123-17-1, 123-18-2, 123-19-3, 123-25-1, 123-29-5, 123-32-0, 123-35-3, 123-51-3, 123-66-0, 123-68-2, 123-69-3, 123-72-8, 123-76-2, 123-86-4, 123-94-4, 123-95-5, 123-96-6, 124-06-1, 124-07-2, 124-10-7, 124-12-9, 124-13-0, 124-18-5, 124-19-6, 124-25-4, 124-76-5, 125-12-2, 126-14-7, 126-64-7, 126-90-9, 126-91-0, 127-25-3, 127-41-3, 127-42-4, 127-42-4, 127-42-4, 127-43-5, 127-51-5, 127-51-5, 127-51-5, 127-51-5, 127-51-5, 127-91-3, 128-37-0, 128-50-7, 128-51-8, 131-11-3, 133-18-6, 134-20-3, 134-28-1, 134-96-3, 135-02-4, 135-79-5, 136-60-7, 137-00-8, 137-03-1, 137-32-6, 138-22-7, 138-23-8, 138-86-3, 138-87-4, 139-45-7, 139-70-8, 140-10-3, 140-11-4, 140-25-0, 140-26-1, 140-27-2, 140-39-6, 140-67-0, 141-03-7, 141-06-0, 141-09-3, 141-11-7, 141-12-8, 141-13-9, 141-14-0, 141-15-1, 141-16-2, 141-25-3, 141-26-4, 141-27-5, 141-28-6, 141-78-6, 141-79-7, 141-92-4, 141-97-9, 142-09-6, 142-19-8, 142-50-7, 142-60-9, 142-62-1, 142-91-6, 142-92-7, 143-07-7, 143-08-8, 143-13-5, 143-14-6, 144-39-8, 150-78-7, 150-84-5, 150-86-7, 151-05-3, 151-10-0, 151-19-9, 156-06-9, 286-99-7, 301-00-8, 326-61-4, 334-48-5, 350-03-8, 409-02-9, 432-24-6, 432-25-7, 459-80-3, 463-40-1, 464-43-7, 464-45-9, 464-48-2, 464-49-3, 469-61-4, 470-67-7, 470-82-6, 470-99-5, 472-64-0, 472-66-2, 472-78-6, 472-97-9, 473-03-0, 473-54-1, 473-55-2, 473-67-6, 475-03-6, 475-20-7, 488-10-8, 488-97-1, 489-40-7, 489-84-9, 489-86-1, 490-03-9, 490-99-3, 491-01-0, 491-02-1, 491-07-6, 491-09-8, 491-35-0, 494-90-6, 495-40-9, 495-61-4, 495-62-5, 495-76-1, 497-03-0, 498-00-0, 498-02-2, 498-16-8, 498-81-7, 499-44-5, 499-54-7, 499-69-4, 499-70-7, 499-75-2, 500-02-7, 501-52-0, 502-26-1, 502-47-6, 502-61-4, 502-69-2, 502-72-7, 502-99-8, 503-74-2, 505-32-8, 506-52-5, 507-70-0, 508-32-7, 511-59-1, 512-13-0, 512-61-8, 513-85-9, 513-86-0, 514-51-2, 514-99-8, 515-00-4, 515-03-7, 515-69-5, 526-75-0, 527-60-6, 527-84-4, 528-79-0, 529-20-4, 529-33-9, 531-26-0, 532-08-1, 533-18-6, 533-31-3, 534-15-6, 535-77-3, 536-50-5, 536-59-4, 536-60-7, 536-75-4, 536-78-7, 538-65-8, 538-86-3, 539-12-8, 539-30-0, 539-82-2, 539-88-8, 539-90-2, 540-07-8, 540-18-1, 540-42-1, 541-85-5, 541-91-3, 542-46-1, 542-55-2, 543-39-5, 543-49-7, 544-12-7, 544-35-4, 544-40-1, 544-63-8, 544-76-3, 546-28-1, 546-49-6, 546-79-2, 546-80-5, 547-60-4, 547-63-7, 551-08-6, 552-02-3, 554-12-1, 555-10-2, 556-24-1, 556-82-1, 557-00-6, 557-48-2, 560-88-3, 562-74-3, 563-80-4, 564-20-5, 564-94-3, 565-62-8, 565-63-9, 576-26-1, 577-16-2, 578-58-5, 579-07-7, 579-74-8, 583-04-0, 583-60-8, 585-24-0, 586-37-8, 586-62-9, 586-82-3, 588-67-0, 589-18-4, 589-35-5, 589-38-8, 589-59-3, 589-66-2, 589-75-3, 589-82-2, 589-98-0, 590-01-2, 590-86-3, 591-11-7, 591-12-8, 591-31-1, 591-47-9, 591-60-6, 591-68-4, 592-20-1, 592-84-7, 592-88-1, 593-08-8, 593-45-3, 600-14-6, 600-18-0, 604-68-2, 606-45-1, 607-85-2, 607-88-5, 607-90-9, 607-97-6, 609-08-5, 611-13-2, 612-16-8, 613-70-7, 614-18-6, 614-34-6, 615-13-4, 616-25-1, 617-01-6, 617-05-0, 617-35-6, 617-50-5, 617-94-7, 618-45-1, 619-01-2, 620-02-0, 620-17-7, 620-23-5, 620-79-1, 620-80-4, 621-82-9, 622-45-7, 623-05-2, 623-17-6, 623-22-3, 623-36-9, 623-37-0, 623-42-7, 623-70-1, 623-84-7, 624-09-9, 624-13-5, 624-15-7, 624-24-8, 624-41-9, 624-51-1, 624-54-4, 624-92-0, 625-55-8, 626-38-0, 626-77-7, 626-82-4, 626-93-7, 627-83-8, 627-90-7, 628-44-4, 628-63-7, 628-73-9, 628-97-7, 628-99-9, 629-19-6, 629-33-4, 629-50-5, 629-59-4, 629-62-9, 629-63-0, 629-78-7, 629-92-5, 629-94-7, 629-96-9, 629-97-0, 634-36-6, 635-46-1, 637-64-9, 637-78-5, 638-11-9, 638-25-5, 638-49-3, 638-53-9, 638-67-5, 639-99-6, 643-53-8, 644-35-9, 644-49-5, 645-13-6, 645-56-7, 645-62-5, 645-72-7, 646-13-9, 656-53-1, 659-70-1, 661-19-8, 670-24-6, 673-84-7, 675-09-2, 687-47-8, 688-82-4, 689-67-8, 692-86-4, 693-54-9, 695-06-7, 697-82-5, 698-10-2, 698-76-0, 699-02-5, 702-23-8, 705-58-8, 705-73-7, 705-86-2, 706-14-9, 707-29-9, 710-04-3, 712-50-5, 713-95-1, 762-26-5, 762-29-8, 763-32-6, 764-39-6, 765-05-9, 765-70-8, 765-87-7, 774-48-1, 774-55-0, 816-19-3, 816-73-9, 818-38-2, 818-81-5, 821-55-6, 823-22-3, 825-51-4, 828-26-2, 831-97-0, 868-57-5, 871-22-7, 874-66-8, 874-90-8, 879-67-4, 881-68-5, 923-69-3, 925-78-0, 928-68-7, 928-80-3, 928-91-6, 928-94-9, 928-95-0, 928-96-1, 928-97-2, 933-48-2, 937-30-4, 939-48-0, 939-97-9, 941-98-0, 943-27-1, 950-33-4, 996-97-4, 999-40-6, 1002-84-2, 1006-27-5, 1011-12-7, 1072-83-9, 1073-11-6, 1073-29-6, 1076-56-8, 1078-95-1, 1079-01-2, 1080-12-2, 1113-21-9, 1114-92-7, 1115-11-3, 1115-84-0, 1117-52-8, 1117-55-1, 1117-59-5, 1117-61-9, 1118-27-0, 1118-39-4, 1119-06-8, 1119-40-0, 1119-44-4, 1122-62-9, 1123-27-9, 1123-85-9, 1124-11-4, 1125-21-9, 1125-88-8, 1128-08-1, 1129-47-1, 1135-66-6, 1139-30-6, 1142-85-4, 1153-51-1, 1166-52-5, 1188-02-9, 1189-09-9, 1191-16-8, 1192-62-7, 1193-18-6, 1193-79-9, 1193-81-3, 1195-32-0, 1195-79-5, 1195-92-2, 1196-01-6, 1196-31-2, 1197-01-9, 1197-15-5, 1197-33-7, 1200-67-5, 1205-17-0, 1205-42-1, 1209-61-6, 1211-29-6, 1217-08-9, 1222-05-5, 1222-05-5, 1222-05-5, 1222-05-5, 1222-05-5, 1222-05-5, 1227-51-6, 1319-88-6, 1321-89-7, 1322-17-4, 1322-58-3, 1323-00-8, 1323-75-7, 1329-99-3, 1330-16-1, 1330-20-7, 1331-81-3, 1331-83-5, 1331-92-6, 1333-09-1, 1333-49-9, 1333-52-4, 1333-53-5, 1333-58-0, 1334-78-7, 1334-82-3, 1335-09-7, 1335-10-0, 1335-12-2, 1335-42-8, 1335-44-0, 1335-46-2, 1335-48-4, 1335-66-6, 1335-86-0, 1337-83-3, 1365-19-1, 1405-92-1, 1406-57-1, 1423-46-7, 1424-83-5, 1438-94-4, 1450-72-2, 1454-84-8, 1490-04-6, 1502-22-3, 1504-55-8, 1504-74-1, 1504-75-2, 1506-02-1, 1516-17-2, 1540-28-9, 1540-29-0, 1551-43-5, 1551-44-6, 1552-67-6, 1561-11-1, 1565-76-0, 1565-81-7, 1569-60-4, 1576-77-8, 1576-78-9, 1576-87-0, 1576-95-0, 1579-21-1, 1585-06-4, 1599-47-9, 1599-49-1, 1604-28-0, 1604-34-8, 1617-23-8, 1629-58-9, 1632-73-1, 1646-26-0, 1653-30-1, 1654-86-0, 1669-44-9, 1670-46-8, 1670-47-9, 1674-08-4, 1708-34-5, 1708-35-6, 1708-36-7, 1708-81-2, 1708-82-3, 1725-01-5, 1728-46-7, 1731-81-3, 1731-84-6, 1731-86-8, 1733-25-1, 1741-41-9, 1754-62-7, 1759-28-0, 1786-08-9, 1797-74-6, 1817-90-9, 1820-09-3, 1838-88-6, 1866-31-5, 1875-89-4, 1879-00-1, 1885-38-7, 1888-90-0, 1900-69-2, 1901-26-4, 1901-38-8, 1922-67-4, 1963-36-6, 1968-40-7, 1975-78-6, 1984-60-7, 2009-74-7, 2021-28-5, 2029-94-9, 2035-99-6, 2040-10-0, 2049-96-9, 2050-01-3, 2050-08-0, 2050-09-1, 2051-78-7, 2051-96-9, 2052-14-4, 2052-15-5, 2057-49-0, 2078-54-8, 2094-69-1, 2094-73-7, 2102-59-2, 2109-22-0, 2110-18-1, 2111-75-3, 2114-29-6, 2114-33-2, 2116-62-3, 2120-70-9, 2120-70-9, 2142-94-1, 2153-26-6, 2153-28-8, 2173-56-0, 2173-57-1, 2177-77-7, 2179-57-9, 2186-92-7, 2198-61-0, 2206-94-2, 2216-45-7, 2216-51-5, 2216-52-6, 2216-81-1, 2217-33-6, 2219-82-1, 2226-05-3, 2239-78-3, 2244-07-7, 2244-16-8, 2257-09-2, 2270-60-2, 2277-16-9, 2277-19-2, 2278-53-7, 2305-05-7, 2305-21-7, 2305-25-1, 2306-78-7, 2306-88-9, 2306-89-0, 2306-91-4, 2308-18-1, 2311-46-8, 2311-59-3, 2315-09-5, 2315-68-6, 2344-70-9, 2345-24-6, 2345-26-8, 2345-27-9, 2345-28-0, 2349-07-7, 2349-13-5, 2351-90-8, 2363-89-5, 2371-13-3, 2380-78-1, 2385-77-5, 2396-77-2, 2396-78-3, 2396-83-0, 2396-84-1, 2396-85-2, 2403-58-9, 2408-20-0, 2408-37-9, 2409-55-4, 2412-73-9, 2412-80-8, 2416-94-6, 2432-51-1, 2432-91-9, 2435-16-7, 2436-90-0, 2437-25-4, 2439-44-3, 2442-10-6, 2445-67-2, 2445-72-9, 2445-76-3, 2445-77-4, 2445-78-5, 2463-53-8, 2463-63-0, 2463-77-6, 2482-39-5, 2497-18-9, 2500-83-6, 2511-00-4, 2520-60-7, 2525-16-8, 2548-87-0, 2550-11-0, 2550-26-7, 2555-49-9, 2556-10-7, 2565-82-4, 2565-83-5, 2568-25-4, 2623-23-6, 2628-17-3, 2630-39-9, 2639-63-6, 2639-68-1, 2679-87-0, 2705-87-5, 2719-08-6, 2721-22-4, 2756-56-1, 2785-87-7, 2785-89-9, 2835-39-4, 2847-30-5, 2882-20-4, 2979-22-8, 2983-36-0, 2983-37-1, 2983-38-2, 2986-54-1, 3008-43-3, 3016-19-1, 3025-30-7, 3033-23-6, 3056-64-2, 3142-72-1, 3149-28-8, 3155-71-3, 3188-00-9, 3208-40-0, 3209-13-0, 3213-73-8, 3239-35-8, 3239-37-0, 3240-09-3, 3240-29-7, 3245-23-6, 3268-49-3, 3269-90-7, 3288-99-1, 3293-47-8, 3301-90-4, 3301-94-8, 3338-55-4, 3360-41-6, 3385-61-3, 3387-41-5, 3390-12-3, 3391-83-1, 3391-86-4, 3391-87-5, 3407-42-9, 3452-97-9, 3460-44-4, 3487-99-8, 3488-00-4, 3491-63-2, 3494-76-6, 3508-98-3, 3521-91-3, 3526-75-8, 3549-23-3, 3558-60-9, 3572-06-3, 3583-00-4, 3603-99-4, 3608-11-5, 3613-30-7, 3623-51-6, 3650-46-2, 3658-77-3, 3658-77-3, 3658-80-8, 3658-93-3, 3681-71-8, 3681-78-5, 3681-82-1, 3683-12-3, 3687-46-5, 3687-48-7, 3691-12-1, 3720-16-9, 3724-54-7, 3724-61-6, 3738-00-9, 3777-69-3, 3777-71-7, 3779-61-1, 3782-00-1, 3796-70-1, 3842-03-3, 3848-24-6, 3891-59-6, 3893-23-0, 3910-35-8, 3913-71-1, 3913-80-2, 3913-81-3, 3915-83-1, 3938-95-2, 3943-74-6, 4077-47-8, 4112-89-4, 4112-92-9, 4125-43-3, 4166-20-5, 4179-19-5, 4180-23-8, 4194-00-7, 4221-98-1, 4230-97-1, 4265-16-1, 4265-97-8, 4312-99-6, 4351-10-4, 4351-54-6, 4353-01-9, 4359-47-1, 4359-57-3, 4360-47-8, 4361-23-3, 4362-22-5, 4364-06-1, 4395-92-0, 4411-89-6, 4427-56-9, 4430-31-3, 4433-36-7, 4437-20-1, 4437-51-8, 4440-65-7, 4442-79-9, 4488-57-7, 4493-42-9, 4501-58-0, 4536-23-6, 4573-50-6, 4602-84-0, 4606-15-9, 4610-11-1, 4621-04-9, 4630-07-3, 4630-82-4, 4643-27-0, 4670-56-8, 4674-50-4, 4675-87-0, 4695-62-9, 4706-81-4, 4707-47-5, 4728-82-9, 4732-13-2, 4740-79-8, 4744-08-5, 4747-07-3, 4748-78-1, 4755-83-3, 4757-23-7, 4798-44-1, 4802-20-4, 4819-67-4, 4826-62-4, 4861-85-2, 4864-61-3, 4884-24-6, 4887-30-3, 4906-24-5, 4927-36-0, 4927-39-3, 4938-52-7, 4941-78-0, 4948-28-1, 4951-48-8, 5077-67-8, 5090-41-5, 5132-75-2, 5137-52-0, 5166-53-0, 5182-36-5, 5205-07-2, 5205-10-7, 5205-11-8, 5208-59-3, 5240-32-4, 5292-21-7, 5320-75-2, 5331-14-6, 5331-32-8, 5333-42-6, 5340-36-3, 5349-51-9, 5349-62-2, 5350-03-8, 5392-40-5, 5392-40-5, 5396-89-4, 5405-41-4, 5405-58-3, 5406-58-6, 5413-60-5, 5421-00-1, 5421-12-5, 5421-17-0, 5421-27-2, 5426-78-8, 5434-57-1, 5435-64-3, 5441-06-5, 5441-56-5, 5442-00-2, 5444-75-7, 5448-22-6, 5451-52-5, 5451-80-9, 5451-85-4, 5451-88-7, 5452-07-3, 5452-75-5, 5454-09-1, 5454-11-5, 5454-19-3, 5454-21-7, 5454-22-8, 5454-28-4, 5457-70-5, 5458-59-3, 5459-98-3, 5461-02-9, 5461-06-3, 5461-08-5, 5462-06-6, 5466-06-8, 5468-05-3, 5468-06-4, 5471-51-2, 5502-75-0, 5524-05-0, 5533-03-9, 5561-08-0, 5579-78-2, 5617-64-1, 5655-61-8, 5660-60-6, 5694-72-4, 5694-82-6, 5703-26-4, 5718-75-2, 5760-50-9, 5764-85-2, 5794-03-6, 5794-04-7, 5820-89-3, 5837-78-5, 5870-68-8, 5870-93-9, 5910-89-4, 5921-82-4, 5932-68-3, 5933-87-9, 5947-36-4, 5949-05-3, 5986-38-9, 5986-55-0, 5988-91-0, 5989-05-9, 5989-27-5, 5989-33-3, 5989-54-8, 6032-29-7, 6051-03-2, 6066-49-5, 6070-14-0, 6090-15-9, 6091-50-5, 6126-50-7, 6132-04-3, 6175-49-1, 6189-76-0, 6191-71-5, 6221-92-7, 6221-93-8, 6222-35-1, 6243-10-3, 6259-76-3, 6259-77-4, 6261-18-3, 6270-03-7, 6281-40-9, 6283-92-7, 6290-17-1, 6290-37-5, 6297-41-2, 6297-48-9, 6309-51-9, 6314-97-2, 6315-04-4, 6324-78-3, 6378-65-0, 6379-73-3, 6380-28-5, 6381-92-6, 6382-06-5, 6382-13-4, 6413-10-1, 6413-26-9, 6414-32-0, 6457-30-3, 6471-66-5, 6485-40-1, 6493-80-7, 6513-03-7, 6561-39-3, 6622-76-0, 6624-71-1, 6635-22-9, 6638-05-7, 6658-48-6, 6707-60-4, 6709-39-3, 6720-16-7, 6728-26-3, 6728-31-0, 6784-08-3, 6784-13-0, 6789-80-6, 6789-88-4, 6790-58-5, 6807-11-0, 6812-78-8, 6819-19-8, 6876-12-6, 6876-13-7, 6901-97-9, 6931-54-0, 6938-45-0, 6939-35-1, 6939-75-9, 6956-37-2, 6963-44-6, 6963-56-0, 6969-49-9, 6976-72-3, 7011-83-8, 7028-48-0, 7053-79-4, 7069-41-2, 7070-15-7, 7111-29-7, 7143-69-3, 7148-78-9, 7149-23-7, 7149-24-8, 7149-26-0, 7149-32-8, 7149-34-0, 7155-12-6, 7158-25-0, 7193-87-5, 7212-40-0, 7212-44-4, 7214-18-8, 7216-56-0, 7289-52-3, 7299-91-4, 7306-12-9, 7335-26-4, 7361-80-0, 7367-78-4, 7367-81-9, 7367-83-1, 7367-84-2, 7367-88-6, 7370-44-7, 7370-92-5, 7384-98-7, 7388-22-9, 7392-19-0, 7399-50-0, 7402-29-1, 7403-42-1, 7416-35-5, 7452-79-1, 7460-74-4, 7491-02-3, 7492-37-7, 7492-39-9, 7492-41-3, 7492-44-6, 7492-45-7, 7492-65-1, 7492-66-2, 7492-67-3, 7492-70-8, 7493-57-4, 7493-58-5, 7493-59-6, 7493-63-2, 7493-65-4, 7493-66-5, 7493-69-8, 7493-72-3, 7493-74-5, 7493-75-6, 7493-76-7, 7493-78-9, 7493-79-0, 7493-80-3, 7493-82-5, 7495-84-3, 7500-42-7, 7504-66-7, 7540-51-4, 7540-53-6, 7541-49-3, 7549-33-9, 7549-37-3, 7549-41-9, 7554-12-3, 7598-60-9, 7732-18-5, 7756-96-9, 7764-50-3, 7774-44-9, 7774-60-9, 7774-65-4, 7774-79-0, 7774-82-5, 7774-96-1, 7775-00-0, 7775-38-4, 7775-39-5, 7778-83-8, 7778-87-2, 7778-96-3, 7779-07-9, 7779-16-0, 7779-17-1, 7779-23-9, 7779-30-8, 7779-41-1, 7779-50-2, 7779-54-6, 7779-65-9, 7779-67-1, 7779-70-6, 7779-72-8, 7779-73-9, 7779-75-1, 7779-77-3, 7779-78-4, 7779-80-8, 7779-81-9, 7779-94-4, 7780-06-5, 7784-67-0, 7784-98-7, 7785-26-4, 7785-33-3, 7785-53-7, 7785-54-8, 7785-64-0, 7785-65-1, 7785-70-8, 7786-29-0, 7786-44-9, 7786-47-2, 7786-48-3, 7786-58-5, 7786-61-0, 7786-67-6, 7787-20-4, 8000-25-7, 8000-25-7, 8000-25-7, 8000-25-7, 8000-25-7, 8000-25-7, 8000-25-7, 8000-25-7, 8000-25-7, 8000-25-7, 8000-25-7, 8000-26-8, 8000-26-8, 8000-26-8, 8000-28-0, 8000-28-0, 8000-28-0, 8000-28-0, 8000-28-0, 8000-28-0, 8000-28-0, 8000-28-0, 8000-28-0, 8000-29-1, 8000-29-1, 8000-29-1, 8000-34-8, 8000-34-8, 8000-34-8, 8000-34-8, 8000-34-8, 8000-34-8, 8000-41-7, 8000-42-8, 8000-42-8, 8000-46-2, 8000-46-2, 8000-46-2, 8000-46-2, 8000-46-2, 8000-48-4, 8000-48-4, 8000-48-4, 8000-48-4, 8000-48-4, 8000-48-4, 8000-66-6, 8000-66-6, 8000-68-8, 8000-68-8, 8000-68-8, 8000-68-8, 8000-78-0, 8000-78-0, 8000-78-0, 8000-78-0, 8001-04-5, 8001-21-6, 8001-25-0, 8001-25-0, 8001-25-0, 8001-25-0, 8001-25-0, 8001-25-0, 8001-26-1, 8001-26-1, 8001-26-1, 8001-31-8, 8001-61-4, 8001-69-2, 8002-09-3, 8002-13-9, 8002-56-0, 8002-60-6, 8002-60-6, 8002-66-2, 8002-66-2, 8002-72-0, 8002-72-0, 8002-72-0, 8002-72-0, 8002-72-0, 8002-73-1, 8002-73-1, 8002-73-1, 8002-73-1, 8002-73-1, 8006-39-1, 8006-64-2, 8006-75-5, 8006-75-5, 8006-75-5, 8006-75-5, 8006-75-5, 8006-75-5, 8006-75-5, 8006-75-5, 8006-77-7, 8006-77-7, 8006-77-7, 8006-77-7, 8006-77-7, 8006-77-7, 8006-77-7, 8006-78-8, 8006-78-8, 8006-81-3, 8006-81-3, 8006-81-3, 8006-81-3, 8006-81-3, 8006-82-4, 8006-82-4, 8006-82-4, 8006-83-5, 8006-84-6, 8006-86-8, 8006-87-9, 8006-87-9, 8006-90-4, 8006-90-4, 8006-90-4, 8006-90-4, 8006-90-4, 8006-90-4, 8006-90-4, 8006-90-4, 8006-90-4, 8006-90-4, 8006-90-4, 8006-90-4, 8006-90-4, 8007-00-9, 8007-00-9, 8007-01-0, 8007-01-0, 8007-01-0, 8007-01-0, 8007-01-0, 8007-01-0, 8007-01-0, 8007-01-0, 8007-02-1, 8007-02-1, 8007-02-1, 8007-04-3, 8007-04-3, 8007-06-5, 8007-08-7, 8007-08-7, 8007-08-7, 8007-08-7, 8007-11-2, 8007-11-2, 8007-11-2, 8007-12-3, 8007-12-3, 8007-20-3, 8007-20-3, 8007-20-3, 8007-35-0, 8007-46-3, 8007-46-3, 8007-46-3, 8007-46-3, 8007-47-4, 8007-47-4, 8007-48-5, 8007-48-5, 8007-70-3, 8007-70-3, 8007-70-3, 8007-70-3, 8007-70-3, 8007-75-8, 8007-75-8, 8007-75-8, 8007-75-8, 8007-75-8, 8007-75-8, 8007-80-5, 8007-80-5, 8007-87-2, 8007-87-2, 8008-26-2, 8008-26-2, 8008-26-2, 8008-26-2, 8008-26-2, 8008-26-2, 8008-26-2, 8008-26-2, 8008-26-2, 8008-26-2, 8008-26-2, 8008-26-2, 8008-26-2, 8008-31-9, 8008-31-9, 8008-31-9, 8008-31-9, 8008-31-9, 8008-31-9, 8008-31-9, 8008-31-9, 8008-31-9, 8008-31-9, 8008-31-9, 8008-31-9, 8008-45-5, 8008-45-5, 8008-45-5, 8008-45-5, 8008-45-5, 8008-51-3, 8008-52-4, 8008-52-4, 8008-52-4, 8008-52-4, 8008-52-4, 8008-56-8, 8008-56-8, 8008-56-8, 8008-56-8, 8008-56-8, 8008-56-8, 8008-56-8, 8008-56-8, 8008-56-8, 8008-56-8, 8008-56-8, 8008-56-8, 8008-56-8, 8008-56-8, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-57-9, 8008-74-0, 8008-74-0, 8008-74-0, 8008-79-5, 8008-79-5, 8008-79-5, 8008-79-5, 8008-80-8, 8008-88-6, 8008-88-6, 8008-93-3, 8008-93-3, 8008-93-3, 8008-93-3, 8008-98-8, 8008-98-8, 8012-89-3, 8012-89-3, 8012-91-7, 8013-12-5, 8013-75-0, 8013-76-1, 8013-90-9, 8013-97-6, 8013-99-8, 8013-99-8, 8014-09-3, 8014-09-3, 8014-09-3, 8014-09-3, 8014-09-3, 8014-13-9, 8014-13-9, 8014-17-3, 8014-17-3, 8014-17-3, 8014-17-3, 8014-17-3, 8014-17-3, 8014-19-5, 8014-29-7, 8014-29-7, 8015-01-8, 8015-01-8, 8015-01-8, 8015-01-8, 8015-62-1, 8015-62-1, 8015-64-3, 8015-64-3, 8015-64-3, 8015-64-3, 8015-64-3, 8015-64-3, 8015-73-4, 8015-73-4, 8015-73-4, 8015-73-4, 8015-73-4, 8015-73-4, 8015-73-4, 8015-73-4, 8015-77-8, 8015-77-8, 8015-77-8, 8015-88-1, 8015-88-1, 8015-88-1, 8015-90-5, 8015-90-5, 8015-90-5, 8015-91-6, 8015-91-6, 8015-91-6, 8015-91-6, 8015-91-6, 8015-91-6, 8015-92-7, 8015-92-7, 8015-92-7, 8016-03-3, 8016-03-3, 8016-03-3, 8016-20-4, 8016-20-4, 8016-20-4, 8016-20-4, 8016-20-4, 8016-20-4, 8016-20-4, 8016-20-4, 8016-20-4, 8016-20-4, 8016-20-4, 8016-20-4, 8016-21-5, 8016-21-5, 8016-21-5, 8016-23-7, 8016-23-7, 8016-26-0, 8016-26-0, 8016-26-0, 8016-26-0, 8016-26-0, 8016-26-0, 8016-31-7, 8016-31-7, 8016-36-2, 8016-36-2, 8016-37-3, 8016-37-3, 8016-37-3, 8016-37-3, 8016-38-4, 8016-38-4, 8016-38-4, 8016-38-4, 8016-42-0, 8016-63-5, 8016-63-5, 8016-63-5, 8016-63-5, 8016-63-5, 8016-63-5, 8016-63-5, 8016-63-5, 8016-63-5, 8016-68-0, 8016-69-1, 8016-78-2, 8016-78-2, 8016-84-0, 8016-84-0, 8016-84-0, 8016-84-0, 8016-84-0, 8016-84-0, 8016-84-0, 8016-84-0, 8016-85-1, 8016-85-1, 8016-85-1, 8016-85-1, 8016-85-1, 8016-88-4, 8016-88-4, 8021-29-2, 8021-39-4, 8022-07-9, 8022-07-9, 8022-07-9, 8022-07-9, 8022-15-9, 8022-15-9, 8022-15-9, 8022-18-2, 8022-56-8, 8022-56-8, 8022-56-8, 8022-56-8, 8022-56-8, 8022-56-8, 8022-56-8, 8022-56-8, 8022-56-8, 8022-96-6, 8022-96-6, 8022-96-6, 8022-96-6, 8022-96-6, 8022-96-6, 8022-96-6, 8022-96-6, 8022-96-6, 8022-96-6, 8022-96-6, 8023-76-5, 8023-78-7, 8023-78-7, 8023-83-4, 8023-83-4, 8023-83-4, 8023-83-4, 8023-89-0, 8023-89-0, 8023-89-0, 8023-91-4, 8023-91-4, 8023-91-4, 8023-99-2, 8023-99-2, 8023-99-2, 8023-99-2, 8024-00-8, 8024-03-1, 8024-05-3, 8024-05-3, 8024-06-4, 8024-06-4, 8024-06-4, 8024-08-6, 8024-08-6, 8024-15-5, 8024-35-9, 8024-40-6, 8028-47-5, 8028-48-6, 8028-48-6, 8028-48-6, 8028-48-6, 8028-48-6, 8028-48-6, 8030-28-2, 8030-28-2, 8030-28-2, 8030-28-2, 8030-55-5, 8030-55-5, 8030-55-5, 8030-89-5, 8030-97-5, 8031-03-6, 8031-03-6, 8031-03-6, 8031-03-6, 8038-65-1, 8038-65-1, 8046-19-3, 8046-22-8, 8046-22-8, 8047-24-3, 8047-24-3, 8048-51-9, 8048-51-9, 8050-07-5, 8050-07-5, 8050-07-5, 8050-15-5, 8052-14-0, 8052-14-0, 8053-33-6, 8053-39-2, 8057-49-6, 8057-49-6, 8057-49-6, 8057-49-6, 8060-28-4, 8060-28-4, 8060-28-4, 8060-28-4, 9000-04-8, 9000-04-8, 9000-05-9, 9000-05-9, 9000-05-9, 9000-05-9, 9000-05-9, 9000-05-9, 9000-12-8, 9000-24-2, 9000-24-2, 9000-24-2, 9000-40-2, 9000-45-7, 9000-45-7, 9000-45-7, 9000-45-7, 9000-45-7, 9000-57-1, 9000-64-0, 9000-64-0, 9000-64-0, 9000-64-0, 9000-72-0, 9000-72-0, 9000-72-0, 9000-72-0, 9000-72-0, 9000-75-3, 9000-75-3, 9000-75-3, 9000-75-3, 9000-78-6, 9000-78-6, 9000-78-6, 9000-78-6, 9005-90-7, 10022-28-3, 10024-56-3, 10024-57-4, 10024-64-3, 10031-71-7, 10031-82-0, 10031-86-4, 10031-87-5, 10031-90-0, 10031-93-3, 10031-96-6, 10032-00-5, 10032-02-7, 10032-05-0, 10032-08-3, 10032-11-8, 10032-13-0, 10032-15-2, 10058-43-2, 10072-05-6, 10094-34-5, 10094-36-7, 10094-40-3, 10094-41-4, 10099-57-7, 10108-80-2, 10138-63-3, 10143-32-5, 10152-77-9, 10198-23-9, 10203-28-8, 10233-13-3, 10235-63-9, 10236-16-5, 10250-45-0, 10276-85-4, 10339-55-6, 10339-61-4, 10340-23-5, 10348-47-7, 10361-39-4, 10402-33-2, 10402-47-8, 10402-52-5, 10411-92-4, 10415-87-9, 10415-88-0, 10444-50-5, 10448-26-7, 10458-14-7, 10471-14-4, 10471-96-2, 10472-24-9, 10482-55-0, 10482-56-1, 10482-65-2, 10482-77-6, 10482-79-8, 10484-09-0, 10484-23-8, 10484-35-2, 10484-36-3, 10484-56-7, 10486-14-3, 10486-19-8, 10519-11-6, 10519-12-7, 10519-33-2, 10521-91-2, 10521-96-7, 10522-26-6, 10522-32-4, 10522-33-5, 10522-41-5, 10544-63-5, 10580-25-3, 10588-10-0, 10588-15-5, 10599-70-9, 11028-42-5, 11031-45-1, 11050-62-7, 12262-03-2, 13002-09-0, 13002-11-4, 13019-22-2, 13058-12-3, 13074-63-0, 13074-65-2, 13109-70-1, 13112-65-7, 13144-88-2, 13171-00-1, 13184-86-6, 13201-46-2, 13215-88-8, 13254-34-7, 13257-44-8, 13262-27-6, 13285-51-3, 13327-56-5, 13341-72-5, 13351-61-6, 13360-65-1, 13380-89-7, 13380-94-4, 13429-07-7, 13442-90-5, 13442-92-7, 13466-78-9, 13477-62-8, 13481-09-9, 13481-87-3, 13487-27-9, 13491-79-7, 13494-06-9, 13494-08-1, 13532-18-8, 13548-84-0, 13552-96-0, 13567-39-0, 13602-09-0, 13623-11-5, 13674-19-6, 13678-59-6, 13679-70-4, 13679-85-1, 13679-86-2, 13708-12-8, 13720-12-2, 13720-13-3, 13786-79-3, 13794-73-5, 13811-71-7, 13816-33-6, 13828-37-0, 13851-06-4, 13851-11-1, 13877-91-3, 13877-93-5, 13894-

61-6, 13894-62-7, 13894-63-8, 13925-00-3, 13925-06-9, 13925-07-0, 13945-76-1, 14049-11-7, 14073-97-3, 14250-95-4, 14289-65-7, 14309-57-0, 14374-92-6, 14436-32-9, 14481-52-8, 14481-55-1, 14576-68-0, 14617-92-6, 14620-52-1, 14667-55-1, 14727-47-0, 14735-72-9, 14765-30-1, 14852-31-4, 14901-07-6, 15103-32-9, 15103-33-0, 15111-56-5, 15111-96-3, 15149-10-7, 15186-51-3, 15323-35-0, 15356-60-2, 15356-74-8, 15373-31-6, 15399-05-0, 15456-70-9, 15514-30-0, 15537-55-0, 15591-90-9, 15679-12-6, 15679-13-7, 15706-73-7, 15707-23-0, 15707-24-1, 15760-18-6, 15764-04-2, 15764-16-6, 15766-66-2, 15932-80-6, 15986-80-8, 16021-08-2, 16251-77-7, 16356-11-9, 16400-72-9, 16409-43-1, 16409-44-2, 16409-45-3, 16409-46-4, 16429-07-5, 16429-21-3, 16491-24-0, 16491-36-4, 16491-54-6, 16493-80-4, 16509-46-9, 16510-27-3, 16556-48-2, 16587-71-6, 16930-93-1, 16930-96-4, 16939-73-4, 16957-70-3, 17102-64-6, 17162-29-7, 17283-81-7, 17369-57-2, 17369-59-4, 17369-60-7, 17373-89-6, 17488-65-2, 17511-60-3, 17511-61-4, 17597-95-4, 17610-24-1, 17627-44-0, 17699-16-0, 17735-99-8, 17909-77-2, 17916-91-5, 18031-40-8, 18096-62-3, 18127-01-0, 18138-04-0, 18172-67-3, 18185-81-4, 18189-02-1, 18189-05-4, 18189-07-6, 18277-27-5, 18294-87-6, 18309-28-9, 18309-32-5, 18339-16-7, 18358-53-7, 18362-97-5, 18368-91-7, 18383-49-8, 18402-82-9, 18409-17-1, 18409-18-2, 18409-21-7, 18433-93-7, 18436-37-8, 18451-96-2, 18479-49-7, 18479-51-1, 18479-54-4, 18479-57-7, 18479-58-8, 18479-58-8, 18479-68-0, 18485-38-6, 18492-65-4, 18492-66-5, 18640-74-9, 18675-16-6, 18675-17-7, 18679-18-0, 18794-84-8, 18824-63-0, 18829-56-6, 18836-52-7, 18871-14-2, 18871-14-2, 19009-56-4, 19089-92-0, 19093-20-0, 19139-31-2, 19141-40-3, 19317-11-4, 19322-27-1, 19329-89-6, 19343-78-3, 19464-94-9, 19487-61-7, 19550-54-0, 19700-21-1, 19781-13-6, 19788-49-9, 19819-98-8, 19870-74-7, 19872-52-7, 19883-29-5, 19902-08-0, 20009-20-5, 20030-30-2, 20053-88-7, 20125-84-2, 20125-85-3, 20273-24-9, 20279-25-8, 20279-43-0, 20279-51-0, 20290-84-0, 20292-09-5, 20298-69-5, 20298-70-8, 20307-84-0, 20407-84-5, 20483-36-7, 20592-10-3, 20662-84-4, 20665-85-4, 20680-10-8, 20691-52-5, 20770-40-5, 20777-39-3, 20777-47-3, 20777-49-5, 20780-48-7, 20780-48-7, 20780-49-8, 20834-59-7, 20859-10-3, 20883-16-3, 20920-83-6, 21016-46-6, 21063-71-8, 21112-37-8, 21129-27-1, 21145-77-7, 21188-58-9, 21188-61-4, 21280-29-5, 21368-68-3, 21653-20-3, 21661-97-2, 21662-09-9, 21662-13-5, 21690-43-7, 21722-83-8, 21834-92-4, 21835-00-7, 21835-01-8, 21862-63-5, 21944-98-9, 21964-44-3, 22009-37-6, 22029-76-1, 22030-19-9, 22037-88-3, 22047-25-2, 22094-00-4, 22104-78-5, 22104-79-6, 22104-80-9, 22104-81-0, 22414-70-6, 22418-66-2, 22451-63-4, 22457-23-4, 22457-25-6, 22460-95-3, 22610-86-2, 22629-48-7, 22629-49-8, 22690-27-3, 22717-57-3, 22719-81-9, 22771-44-4, 22810-10-2, 22874-79-9, 22882-89-9, 22882-91-3, 23089-26-1, 23147-57-1, 23267-57-4, 23333-91-7, 23361-88-8, 23495-12-7, 23511-70-8, 23550-40-5, 23696-85-7, 23726-91-2, 23726-92-3, 23726-93-4, 23726-94-5, 23733-88-2, 23747-48-0, 23787-90-8, 23832-18-0, 23950-98-3, 23985-25-3, 23986-74-5, 24048-13-3, 24048-14-4, 24089-00-7, 24168-70-5, 24202-00-4, 24237-00-1, 24237-01-2, 24237-02-3, 24238-95-7, 24295-03-2, 24317-94-0, 24323-38-4, 24650-42-8, 24680-50-0, 24683-00-9, 24691-15-4, 24691-17-6, 24700-20-7, 24717-85-9, 24717-86-0, 24720-09-0, 24817-51-4, 24851-98-7, 25013-16-5, 25152-85-6, 25225-08-5, 25225-09-6, 25225-10-9, 25226-98-6, 25263-97-2, 25265-71-8, 25279-09-8, 25304-14-7, 25312-34-9, 25334-93-4, 25339-17-7, 25340-17-4, 25395-31-7, 25415-62-7, 25415-67-2, 25415-77-4, 25435-63-6, 25524-95-2, 25628-84-6, 25680-58-4, 25773-40-4, 25905-14-0, 25966-79-4, 26001-58-1, 26160-83-8, 26171-78-8, 26252-11-9, 26330-64-3, 26330-65-4, 26370-28-5, 26446-31-1, 26446-32-2, 26489-01-0, 26537-19-9, 26553-46-8, 26619-69-2, 26643-91-4, 26643-92-5, 26896-48-0, 26952-21-6, 27039-84-5, 27043-05-6, 27135-90-6, 27178-16-1, 27196-00-5, 27310-22-1, 27458-92-0, 27458-94-2, 27538-09-6, 27538-10-9, 27539-94-2, 27575-61-7, 27593-23-3, 27606-09-3, 27625-35-0, 27829-72-7, 27939-60-2, 28043-10-9, 28060-90-4, 28069-72-9, 28069-74-1, 28132-01-6, 28219-60-5, 28219-61-6, 28231-03-0, 28267-32-5, 28290-90-6, 28369-24-6, 28371-99-5, 28387-62-4, 28462-85-3, 28588-74-1, 28645-51-4, 28664-35-9, 28787-36-2, 28839-13-6, 28897-20-3, 28897-58-7, 28940-11-6, 28959-02-6, 28977-58-4, 29021-36-1, 29066-34-0, 29127-83-1, 29171-20-8, 29171-21-9, 29210-77-3, 29214-60-6, 29239-07-4, 29350-67-2, 29350-73-0, 29460-92-2, 29461-13-0, 29548-14-9, 29548-30-9, 29592-92-5, 29592-95-8, 29606-79-9, 29714-87-2, 29759-11-3, 29806-73-3, 29811-50-5, 29895-73-6, 29896-45-5, 29957-43-5, 30076-98-3, 30100-15-3, 30168-23-1, 30207-98-8, 30310-41-9, 30390-50-2, 30390-51-3, 30418-89-4, 30460-92-5, 30640-46-1, 30673-36-0, 30673-38-2, 30673-60-0, 30772-69-1, 30772-79-3, 30895-79-5, 30897-75-7, 30960-39-5, 30982-03-7, 31147-36-1, 31148-31-9, 31161-71-4, 31308-55-1, 31375-17-4, 31499-72-6, 31501-11-8, 31502-14-4, 31502-19-9, 31565-19-2, 31574-44-4, 31795-37-6, 31807-55-3, 31846-06-7, 31906-04-4, 31996-78-8, 32074-56-9, 32210-23-4, 32214-91-8, 32388-55-9, 32388-56-0, 32438-31-6, 32466-55-0, 32659-21-5, 32665-23-9, 32737-14-7, 32741-11-0, 32764-98-0, 32797-50-5, 32803-39-7, 32974-92-8, 33046-81-0, 33079-56-0, 33281-91-3, 33467-73-1, 33467-74-2, 33467-74-2, 33467-76-4, 33662-58-7, 33673-62-0, 33673-65-3, 33673-71-1, 33704-60-8, 33704-61-9, 33880-83-0, 33885-51-7, 33885-52-8, 33900-84-4, 33941-99-0, 34131-98-1, 34291-99-1, 34316-64-8, 34322-06-0, 34322-08-2, 34322-09-3, 34365-79-2, 34413-35-9, 34451-19-9, 34495-71-1, 34545-88-5, 34590-94-8, 34686-71-0, 34687-43-9, 34764-02-8, 34962-91-9, 34995-77-2, 35044-57-6, 35044-58-7, 35044-59-8, 35044-63-4, 35044-68-9, 35061-61-1, 35127-50-5, 35151-11-2, 35154-45-1, 35158-25-9, 35205-76-6, 35206-51-0, 35234-21-0, 35234-25-4, 35274-05-6, 35472-56-1, 35670-93-0, 35720-57-1, 35852-46-1, 35854-86-5, 36208-32-9, 36219-73-5, 36267-71-7, 36306-86-2, 36306-87-3, 36399-15-2, 36431-72-8, 36438-54-7, 36528-28-6, 36653-82-4, 36685-97-9, 36789-59-0, 37064-20-3, 37161-74-3, 37172-02-4, 37172-05-7, 37172-53-5, 37172-54-6, 37514-30-0, 37526-88-8, 37596-36-4, 37609-25-9, 37617-03-1, 37674-63-8, 37677-14-8, 37811-72-6, 37837-44-8, 37973-51-6, 37973-52-7, 38019-89-5, 38049-26-2, 38142-45-9, 38228-51-2, 38237-00-2, 38285-49-3, 38303-23-0, 38446-21-8, 38462-22-5, 38462-23-6, 38533-54-9, 38618-23-4, 38713-41-6, 38888-81-2, 39026-94-3, 39067-39-5, 39067-80-6, 39129-16-3, 39189-74-7, 39212-23-2, 39251-86-0, 39255-32-8, 39282-36-5, 39556-41-7, 39770-04-2, 39770-05-3, 39864-15-8, 39872-57-6, 39900-12-4, 39900-38-4, 39924-27-1, 39924-52-2, 40188-41-8, 40203-73-4, 40267-72-9, 40379-24-6, 40527-42-2, 40596-76-7, 40654-82-8, 40702-13-4, 40716-66-3, 40785-62-4, 40853-53-0, 40853-56-3, 40910-49-4, 40923-64-6, 40942-73-2, 41199-19-3, 41199-19-3, 41270-80-8, 41414-75-9, 41448-29-7, 41453-56-9, 41496-43-9, 41519-18-0, 41519-23-7, 41547-22-2, 41654-15-3, 41678-36-8, 41723-98-2, 41724-19-0, 41767-05-9, 41816-03-9, 41847-86-3, 41847-88-5, 41890-92-0, 41927-71-3, 42075-45-6, 42078-65-9, 42175-41-7, 42231-50-5, 42231-99-2, 42232-27-9, 42288-75-5, 42348-12-9, 42370-06-9, 42370-07-0, 42436-07-7, 42604-12-6, 42822-86-6, 42822-86-6, 42824-62-4, 42866-91-1, 43052-87-5, 45019-

28-1, 50343-36-7, 50373-36-9, 50405-95-3, 50542-90-0, 50607-64-2, 50623-57-9, 50638-95-4, 50816-18-7, 50980-84-2, 51015-28-2, 51015-29-3, 51100-54-0, 51115-63-0, 51115-64-1, 51115-67-4, 51115-88-9, 51117-19-2, 51200-86-3, 51352-68-2, 51411-24-6, 51414-25-6, 51447-08-6, 51519-65-4, 51532-26-4, 51534-36-2, 51556-30-0, 51566-62-2, 51595-91-6, 51608-18-5, 51685-39-3, 51685-40-6, 51755-66-9, 51755-83-0, 51755-85-2, 51756-08-2, 52089-55-1, 52191-01-2, 52210-18-1, 52363-43-6, 52474-60-9, 52475-86-2, 52475-89-5, 52514-66-6, 52517-67-6, 52557-97-8, 52788-71-3, 52972-16-4, 53004-93-6, 53018-24-9, 53046-97-2, 53082-58-9, 53153-67-6, 53179-04-7, 53219-21-9, 53243-59-7, 53243-60-0, 53338-05-9, 53338-06-0, 53398-78-0, 53398-80-4, 53398-81-5, 53398-83-7, 53398-84-8, 53398-85-9, 53398-86-0, 53398-87-1, 53399-81-8, 53405-97-3, 53405-98-4, 53446-63-2, 53448-07-0, 53452-65-6, 53488-14-5, 53498-32-1, 53535-33-4, 53751-40-9, 53767-86-5, 53767-93-4, 53834-70-1, 53889-39-7, 54043-73-1, 54082-68-7, 54089-83-7, 54200-50-9, 54300-08-2, 54300-09-3, 54300-10-6, 54340-90-8, 54393-36-1, 54410-94-5, 54440-17-4, 54464-57-2, 54464-59-4, 54484-73-0, 54491-17-7, 54533-29-8, 54546-26-8, 54653-25-7, 54815-13-3, 54830-99-8, 54852-64-1, 54889-48-4, 54947-74-9, 54982-83-1, 54992-91-5, 54993-30-5, 55050-40-3, 55066-48-3, 55066-49-4, 55066-53-0, 55066-54-1, 55066-56-3, 55418-52-5, 55505-28-7, 55514-48-2, 55704-78-4, 55719-85-2, 55722-59-3, 55881-96-4, 55915-70-3, 56001-43-5, 56011-02-0, 56057-93-3, 56105-46-5, 56107-04-1, 56134-05-5, 56172-46-4, 56423-40-6, 56423-43-9, 56438-09-6, 56469-39-7, 56747-96-7, 56805-23-3, 56836-93-2, 56922-74-8, 56922-81-7, 56922-82-8, 56961-73-0, 56973-85-4, 57069-86-0, 57069-87-1, 57074-34-7, 57074-37-0, 57082-24-3, 57094-40-3, 57129-12-1, 57246-60-3, 57345-19-4, 57371-42-3, 57378-68-4, 57500-00-2, 57568-60-2, 57576-09-7, 57582-46-4, 57743-63-2, 57856-81-2, 57893-27-3, 57934-97-1, 57943-67-6, 57967-68-7, 57967-72-3, 57967-73-4, 57967-74-5, 58001-88-0, 58031-03-1, 58096-46-1, 58096-47-2, 58102-02-6, 58206-95-4, 58214-96-3, 58243-85-9, 58244-29-4, 58260-78-9, 58296-81-4, 58430-94-7, 58437-69-7, 58461-27-1, 58475-04-0, 58479-55-3, 58555-74-1, 58567-11-6, 58625-95-9, 58625-96-0, 58911-05-0, 58927-81-4, 58985-02-7, 58985-18-5, 59020-90-5, 59052-82-3, 59056-62-1, 59056-64-3, 59056-70-1, 59151-19-8, 59191-78-5, 59230-57-8, 59259-38-0, 59259-90-4, 59323-76-1, 59324-17-3, 59354-71-1, 59376-58-8, 59471-80-6, 59558-23-5, 59632-85-8, 59672-05-8, 60045-26-3, 60045-27-4, 60047-17-8, 60066-88-8, 60113-43-1, 60160-17-0, 60234-72-2, 60241-52-3, 60241-53-4, 60241-55-6, 60308-75-0, 60308-76-1, 60335-71-9, 60405-50-7, 60415-61-4, 60523-21-9, 60763-40-8, 60763-41-9, 60763-42-0, 60763-44-2, 60770-00-5, 60788-25-2, 60826-15-5, 60958-23-8, 61099-53-4, 61114-24-7, 61415-11-0, 61444-38-0, 61444-39-1, 61444-41-5, 61531-45-1, 61683-99-6, 61692-78-2, 61692-83-9, 61692-84-0, 61699-38-5, 61702-91-8, 61758-03-0, 61759-64-6, 61789-53-5, 61789-92-2, 61789-92-2, 61789-92-2, 61789-92-2, 61792-11-8, 61792-12-9, 61810-55-7, 61826-52-6, 61826-53-7, 61826-56-0, 61920-45-4, 61931-80-4, 61931-81-5, 61949-23-3, 62062-85-5, 62151-56-8, 62346-96-7, 62395-45-3, 62406-73-9, 62439-41-2, 62488-24-8, 62488-56-6, 62501-24-0, 62518-65-4, 62563-80-8, 63095-33-0, 63187-91-7, 63253-24-7, 63270-14-4, 63429-28-7, 63449-64-9, 63449-68-3, 63449-88-7, 63449-89-8, 63449-95-6, 63450-30-6, 63500-71-0, 63649-51-4, 63826-25-5, 63885-09-6, 64001-15-6, 64165-57-7, 64187-83-3, 64275-73-6, 64461-99-0, 64577-91-9, 64644-32-2, 64644-34-4, 64644-36-6, 64825-20-3, 64988-06-3, 65113-95-3, 65113-99-7, 65114-03-6, 65155-45-5, 65405-67-6, 65405-68-7, 65405-69-8, 65405-70-1, 65405-72-3, 65405-73-4, 65405-76-7, 65405-77-8, 65405-80-3, 65405-84-7, 65416-14-0, 65416-17-3, 65416-20-8, 65416-21-9, 65416-26-4, 65442-31-1, 65443-14-3, 65505-24-0, 65505-25-1, 65530-53-2, 65620-50-0, 65652-28-0, 65652-33-7, 65737-52-2, 65813-53-8, 65996-98-7, 65996-99-8, 65997-06-0, 66008-65-9, 66008-66-0, 66062-78-0, 66068-84-6, 66072-32-0, 66327-54-6, 66408-78-4, 66471-49-6, 66576-71-4, 66848-40-6, 66848-41-7, 67019-89-0, 67028-40-4, 67114-38-9, 67234-04-2, 67355-38-8, 67392-15-8, 67452-27-1, 67583-77-1, 67601-05-2, 67633-92-5, 67633-93-6, 67633-94-7, 67633-95-8, 67633-96-9, 67633-98-1, 67633-99-2, 67634-00-8, 67634-01-9, 67634-02-0, 67634-03-1, 67634-04-2, 67634-05-3, 67634-06-4, 67634-07-5, 67634-08-6, 67634-09-7, 67634-11-1, 67634-12-2, 67634-14-4, 67634-15-5, 67634-16-6, 67634-17-7, 67634-20-2, 67634-22-4, 67634-23-5, 67634-24-6, 67634-25-7, 67634-26-8, 67662-96-8, 67663-01-8, 67663-03-0, 67663-05-2, 67674-36-6, 67674-37-7, 67674-41-3, 67674-46-8, 67674-47-9, 67689-50-3, 67701-33-1, 67707-75-9, 67710-71-8, 67715-79-1, 67715-80-4, 67715-81-5, 67715-82-6, 67770-79-0, 67785-69-7, 67785-71-1, 67785-76-6, 67785-77-7, 67800-80-0, 67800-86-6, 67801-16-5, 67801-17-6, 67801-20-1, 67801-23-4, 67801-27-8, 67801-29-0, 67801-30-3, 67801-31-4, 67801-32-5, 67801-33-6, 67801-36-9, 67801-37-0, 67801-38-1, 67801-39-2, 67801-40-5, 67801-41-6, 67801-42-7, 67801-43-8, 67801-44-9, 67801-45-0, 67801-46-1, 67801-47-2, 67801-64-3, 67801-65-4, 67828-19-7, 67845-30-1, 67845-42-5, 67845-46-9, 67845-50-5, 67845-58-3, 67845-59-4, 67859-96-5, 67860-00-8, 67860-01-9, 67874-67-3, 67874-68-4, 67874-69-5, 67874-72-0, 67874-73-1, 67874-74-2, 67874-77-5, 67874-78-6, 67874-80-0, 67874-81-1, 67883-79-8, 67890-79-3, 67905-40-2, 67919-67-9, 67920-63-2, 67920-94-9, 67923-79-9, 67923-82-4, 67923-83-5, 67923-84-6, 67923-85-7, 67923-86-8, 67924-13-4, 67924-14-5, 67952-57-2, 67952-65-2, 67952-68-5, 67999-56-8, 67999-56-8, 68039-24-7, 68039-26-9, 68039-34-9, 68039-35-0, 68039-38-3, 68039-39-4, 68039-40-7, 68039-41-8, 68039-42-9, 68039-44-1, 68039-45-2, 68039-47-4, 68039-48-5, 68039-49-6, 68039-69-0, 68039-73-6, 68039-78-1, 68071-23-8, 68083-54-5, 68083-55-6, 68083-57-8, 68083-58-9, 68084-04-8, 68092-41-1, 68129-81-7, 68132-21-8, 68132-80-9, 68133-72-2, 68133-73-3, 68133-74-4, 68133-75-5, 68133-76-6, 68133-77-7, 68133-78-8, 68133-79-9, 68140-48-7, 68140-52-3, 68141-11-7, 68141-13-9, 68141-14-0, 68141-17-3, 68141-18-4, 68141-19-5, 68141-20-8, 68141-26-4, 68141-27-5, 68153-06-0, 68155-66-8, 68155-67-9, 68186-14-1, 68188-98-7, 68198-80-1, 68213-85-4, 68213-86-5, 68213-87-6, 68214-06-2, 68228-06-8, 68228-09-1, 68228-10-4, 68228-11-5, 68258-95-7, 68259-31-4, 68259-33-6, 68298-28-2, 68298-33-9, 68298-48-6, 68310-59-8, 68311-05-7, 68345-17-5, 68345-22-2, 68378-13-2, 68391-29-7, 68391-39-9, 68398-16-3, 68398-18-5, 68411-59-6, 68412-04-4, 68419-46-5, 68433-81-8, 68458-86-6, 68459-95-0, 68459-99-4, 68478-36-4, 68479-99-2, 68480-04-6, 68480-05-7, 68480-06-8, 68480-07-9, 68480-08-0, 68480-10-4, 68480-11-5, 68480-12-6, 68480-14-8, 68480-15-9, 68480-17-1, 68480-21-7, 68480-25-1, 68480-26-2, 68480-27-3, 68480-28-4, 68516-18-7, 68526-83-0, 68526-84-1, 68526-85-2, 68526-86-3, 68526-90-9, 68527-05-9, 68527-06-0, 68527-74-2, 68527-76-4, 68527-77-5, 68527-78-6, 68527-79-7, 68527-82-2, 68553-81-1, 68553-81-1, 68555-28-2, 68555-31-7, 68555-53-3, 68555-57-7, 68555-58-8, 68555-59-9, 68555-61-3, 68555-62-4, 68555-63-5, 68555-64-6, 68555-65-7, 68555-94-2, 68555-95-3, 68585-09-1, 68602-86-8, 68606-81-5, 68606-81-5, 68606-81-5, 68606-81-5, 68606-81-5, 68606-82-6, 68606-83-7, 68606-

83-7, 68606-94-0, 68606-94-0, 68606-97-3, 68606-97-3, 68607-01-2, 68611-23-4, 68648-33-9, 68648-39-5, 68650-43-1, 68650-43-1, 68650-44-2, 68650-46-4, 68683-20-5, 68683-22-7, 68683-25-0, 68698-57-7, 68698-59-9, 68705-63-5, 68738-94-3, 68738-96-5, 68738-96-5, 68738-99-8, 68797-68-2, 68804-00-2, 68804-02-4, 68844-95-1, 68844-96-2, 68844-97-3, 68845-00-1, 68845-01-2, 68845-02-3, 68845-33-0, 68845-35-2, 68845-36-3, 68855-38-9, 68855-99-2, 68877-29-2, 68891-95-2, 68901-15-5, 68901-22-4, 68901-32-6, 68901-32-6, 68907-19-7, 68908-82-7, 68909-04-6, 68911-60-4, 68911-60-4, 68912-13-0, 68915-85-5, 68916-02-9, 68916-04-1, 68916-04-1, 68916-04-1, 68916-04-1, 68916-04-1, 68916-05-2, 68916-07-4, 68916-18-7, 68916-18-7, 68916-26-7, 68916-26-7, 68916-26-7, 68916-26-7, 68916-45-0, 68916-45-0, 68916-46-1, 68916-54-1, 68916-76-7, 68916-76-7, 68916-84-7, 68916-84-7, 68916-84-7, 68916-89-2, 68916-91-6, 68917-05-5, 68917-10-2, 68917-18-0, 68917-18-0, 68917-18-0, 68917-18-0, 68917-20-4, 68917-46-4, 68917-50-0, 68917-52-2, 68917-52-2, 68917-52-2, 68917-63-5, 68917-75-9, 68921-26-6, 68922-09-8, 68922-10-1, 68922-11-2, 68922-12-3, 68922-13-4, 68928-61-0, 68937-31-5, 68937-84-8, 68938-00-1, 68952-43-2, 68952-43-2, 68956-56-9, 68956-68-3, 68959-28-4, 68966-86-9, 68989-91-3, 68990-11-4, 68990-11-4, 68990-11-4, 68990-11-4, 68990-11-4, 68990-15-8, 68990-15-8, 68990-66-9, 68991-20-8, 68991-95-7, 68991-96-8, 68991-97-9, 69038-78-4, 69102-96-1, 69103-01-1, 69103-20-4, 69103-23-7, 69103-24-8, 69178-43-4, 69300-15-8, 69834-10-2, 69882-09-3, 69925-33-3, 69929-16-4, 69929-17-5, 70092-23-8, 70131-51-0, 70214-77-6, 70788-30-6, 70851-60-4, 70851-61-5, 70892-20-5, 70892-62-5, 70955-71-4, 71011-28-4, 71048-82-3, 71077-30-0, 71077-31-1, 71078-31-4, 71159-90-5, 71172-26-4, 71172-75-3, 71298-42-5, 71500-37-3, 71566-53-5, 71605-84-0, 71605-85-1, 71617-09-9, 71617-11-3, 71648-16-3, 71648-18-5, 71648-34-5, 71648-43-6, 71662-17-4, 71662-25-4, 71662-26-5, 71735-79-0, 71820-51-4, 71832-76-3, 71850-78-7, 71850-80-1, 71949-33-2, 71990-22-2, 72007-81-9, 72089-08-8, 72175-33-8, 72183-75-6, 72214-23-4, 72214-33-6, 72402-00-7, 72403-67-9, 72429-08-4, 72779-06-7, 72785-17-2, 72797-17-2, 72812-40-9, 72845-33-1, 72845-85-3, 72854-42-3, 72869-31-9, 72869-69-3, 72869-70-6, 72881-27-7, 72894-07-6, 72894-11-2, 72894-12-3, 72894-13-4, 72894-14-5, 72894-15-6, 72928-35-9, 72928-45-1, 72928-47-3, 72928-51-9, 72928-52-0, 72934-06-6, 72934-07-7, 72934-16-8, 72968-25-3, 72968-30-0, 72968-47-9, 72968-50-4, 72968-50-4, 72968-50-4, 72968-50-4, 72968-50-4, 72968-50-4, 72968-50-4, 72968-69-5, 72987-59-8, 73003-91-5, 73018-51-6, 73019-14-4, 73049-51-1, 73138-66-6, 73263-36-2, 73296-98-7, 73296-98-7, 73347-77-0, 73360-66-4, 73398-85-3, 73507-35-4, 73545-18-3, 73545-19-4, 73952-68-8, 74094-60-3, 74094-61-4, 74094-62-5, 74094-63-6, 74113-74-9, 74298-89-8, 74367-97-8, 74499-58-4, 74499-60-8, 74585-00-5, 74912-37-1, 74962-98-4, 75039-84-8, 75048-15-6, 75147-23-8, 75490-39-0, 75587-06-3, 76238-22-7, 76649-14-4, 76649-16-6, 76649-17-7, 76649-22-4, 76649-23-5, 76649-24-6, 76649-25-7, 76649-26-8, 76788-46-0, 77129-48-7, 77851-07-1, 78417-28-4, 78548-53-5, 78649-62-4, 78989-37-4, 79893-63-3, 79915-74-5, 79930-37-3, 80118-06-5, 80118-10-1, 80314-58-5, 80417-97-6, 80480-24-6, 80657-64-3, 80858-47-5, 80866-83-7, 81782-77-6, 81782-89-0, 81783-01-9, 81786-73-4, 81786-74-5, 81786-75-6, 81836-13-7, 81836-17-1, 81925-81-7, 81974-61-0, 82185-41-9, 82356-51-2, 82461-14-1, 82654-98-6, 82784-84-7, 83334-93-4, 83846-55-3, 83863-22-3, 83863-30-3, 83863-30-3, 83863-30-3, 83863-32-5, 83863-64-3, 83926-73-2, 83984-76-3, 83984-78-5, 84012-14-6, 84012-15-7, 84012-15-7, 84012-15-7, 84012-21-5, 84012-24-8, 84012-24-8, 84012-28-2, 84012-30-6, 84012-33-9, 84012-33-9, 84012-33-9, 84012-34-0, 84012-35-1, 84012-35-1, 84012-35-1, 84012-35-1, 84012-35-1, 84012-35-1, 84012-35-1, 84012-39-5, 84012-43-1, 84012-44-2, 84012-44-2, 84012-44-2, 84012-64-6, 84029-90-3, 84029-92-5, 84029-93-6, 84041-80-5, 84060-80-0, 84082-34-8, 84082-36-0, 84082-36-0, 84082-54-2, 84082-58-6, 84082-58-6, 84082-58-6, 84082-58-6, 84082-58-6, 84082-58-6, 84082-60-0, 84082-60-0, 84082-60-0, 84082-60-0, 84082-60-0, 84082-60-0, 84082-61-1, 84082-62-2, 84082-67-7, 84082-67-7, 84082-67-7, 84082-68-8, 84082-68-8, 84082-68-8, 84082-68-8, 84082-68-8, 84082-70-2, 84082-70-2, 84082-70-2, 84082-70-2, 84082-70-2, 84082-70-2, 84082-79-1, 84082-79-1, 84082-79-1, 84082-79-1, 84082-79-1, 84082-79-1, 84082-80-4, 84082-80-4, 84082-80-4, 84082-81-5, 84082-81-5, 84082-81-5, 84082-81-5, 84082-83-7, 84082-83-7, 84082-84-8, 84238-19-7, 84238-29-9, 84238-39-1, 84238-39-1, 84238-39-1, 84254-89-7, 84434-18-4, 84434-20-8, 84434-64-0, 84434-65-1, 84455-19-6, 84455-19-6, 84455-19-6, 84455-19-6, 84455-19-6, 84455-29-8, 84455-29-8, 84560-00-9, 84603-58-7, 84603-58-7, 84603-58-7, 84603-58-7, 84603-58-7, 84603-60-1, 84603-61-2, 84603-62-3, 84603-62-3, 84603-66-7, 84603-66-7, 84603-66-7, 84603-69-0, 84603-69-0, 84603-69-0, 84603-69-0, 84603-69-0, 84603-69-0, 84603-73-6, 84603-73-6, 84603-73-6, 84604-07-9, 84604-07-9, 84604-07-9, 84604-07-9, 84604-12-6, 84604-12-6, 84604-12-6, 84604-12-6, 84604-12-6, 84604-12-6, 84604-12-6, 84604-12-6, 84604-13-7, 84604-13-7, 84604-13-7, 84604-13-7, 84604-13-7, 84604-14-8, 84604-14-8, 84604-14-8, 84604-14-8, 84604-14-8, 84604-14-8, 84604-14-8, 84604-14-8, 84604-14-8, 84604-17-1, 84625-26-3, 84625-26-3, 84625-29-6, 84625-32-1, 84625-32-1, 84625-32-1, 84625-36-5, 84625-39-8, 84625-40-1, 84625-40-1, 84625-40-1, 84625-40-1, 84625-40-1, 84625-40-1, 84642-57-9, 84642-60-4, 84649-81-0, 84649-86-5, 84649-86-5, 84649-86-5, 84649-93-4, 84649-93-4, 84649-93-4, 84649-96-7, 84649-96-7, 84649-97-8, 84649-97-8, 84649-97-8, 84649-98-9, 84649-98-9, 84649-98-9, 84649-98-9, 84649-99-0, 84649-99-0, 84649-99-0, 84650-00-0, 84650-00-0, 84650-00-0, 84650-00-0, 84650-00-0, 84650-00-0, 84650-00-0, 84650-00-0, 84650-00-0, 84650-05-5, 84650-10-2, 84650-11-3, 84650-13-5, 84650-13-5, 84650-13-5, 84650-13-5, 84650-39-5, 84650-39-5, 84650-55-5, 84650-59-9, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-60-2, 84650-63-5, 84681-92-5, 84682-20-2, 84695-96-5, 84696-05-9, 84696-07-1, 84696-07-1, 84696-07-1, 84696-07-1, 84696-07-1, 84696-07-1, 84696-10-6, 84696-13-9, 84696-13-9, 84696-13-9, 84696-15-1, 84696-15-1, 84696-15-1, 84696-15-1, 84696-19-5, 84696-24-2, 84696-24-2, 84696-27-5, 84696-27-5, 84696-47-9, 84696-51-5, 84696-51-5, 84696-51-5, 84696-51-5, 84696-51-5, 84696-53-7, 84697-09-6, 84712-50-5, 84775-39-3, 84775-39-3, 84775-39-3, 84775-39-3, 84775-39-3, 84775-39-3, 84775-41-7, 84775-41-7, 84775-41-7, 84775-41-7, 84775-41-7, 84775-41-7, 84775-41-7, 84775-42-8, 84775-42-8, 84775-45-1, 84775-45-1, 84775-50-8, 84775-50-8, 84775-50-8, 84775-50-8, 84775-50-8, 84775-50-8, 84775-51-9, 84775-52-0, 84775-52-0, 84775-52-0, 84775-53-1, 84775-64-4, 84775-64-4, 84775-64-4, 84775-64-4, 84775-66-6, 84775-66-6, 84775-66-6, 84775-66-6, 84775-66-6, 84775-66-6, 84775-70-2, 84775-70-2, 84775-70-2, 84775-70-2, 84775-70-2, 84775-70-2, 84775-70-2, 84775-70-2, 84775-70-2, 84775-71-3, 84775-71-3, 84775-71-3, 84775-

71-3, 84775-71-3, 84775-73-5, 84775-74-6, 84775-74-6, 84775-74-6, 84775-74-6, 84775-74-6, 84775-74-6, 84775-80-4, 84775-80-4, 84775-83-7, 84775-83-7, 84775-83-7, 84775-83-7, 84775-83-7, 84775-83-7, 84775-96-2, 84775-98-4, 84776-10-3, 84776-23-8, 84776-23-8, 84776-23-8, 84776-64-7, 84776-64-7, 84776-65-8, 84776-67-0, 84776-98-7, 84776-98-7, 84776-98-7, 84776-98-7, 84776-98-7, 84776-98-7, 84776-98-7, 84787-69-9, 84787-69-9, 84787-70-2, 84787-70-2, 84787-70-2, 84788-08-9, 84836-94-2, 84836-99-7, 84837-04-7, 84837-06-9, 84837-06-9, 84837-06-9, 84837-08-1, 84837-14-9, 84929-19-1, 84929-19-1, 84929-26-0, 84929-26-0, 84929-26-0, 84929-26-0, 84929-27-1, 84929-28-2, 84929-31-7, 84929-31-7, 84929-31-7, 84929-31-7, 84929-31-7, 84929-35-1, 84929-38-4, 84929-38-4, 84929-38-4, 84929-41-9, 84929-41-9, 84929-47-5, 84929-47-5, 84929-47-5, 84929-51-1, 84929-51-1, 84929-51-1, 84929-51-1, 84929-51-1, 84929-52-2, 84929-52-2, 84929-57-7, 84929-61-3, 84929-61-3, 84929-61-3, 84929-61-3, 84929-61-3, 84929-76-0, 84929-76-0, 84929-78-2, 84929-78-2, 84929-78-2, 84929-79-3, 84929-79-3, 84961-45-5, 84961-45-5, 84961-45-5, 84961-45-5, 84961-45-5, 84961-45-5, 84961-46-6, 84961-46-6, 84961-46-6, 84961-46-6, 84961-46-6, 84961-46-6, 84961-49-9, 84961-49-9, 84961-49-9, 84961-50-2, 84961-50-2, 84961-50-2, 84961-50-2, 84961-50-2, 84961-50-2, 84961-57-9, 84961-57-9, 84961-62-6, 84961-62-6, 84961-64-8, 84961-64-8, 84961-64-8, 84961-64-8, 84961-64-8, 84961-64-8, 84961-66-0, 84961-66-0, 84961-67-1, 84961-67-1, 84961-67-1, 84961-67-1, 84988-66-9, 84988-66-9, 84988-66-9, 84988-87-4, 85085-29-6, 85085-29-6, 85085-34-3, 85085-34-3, 85085-41-2, 85085-43-4, 85085-46-7, 85085-47-8, 85085-48-9, 85085-48-9, 85085-48-9, 85085-49-0, 85085-49-0, 85085-54-7, 85085-61-6, 85085-68-3, 85085-69-4, 85085-75-2, 85085-75-2, 85085-75-2, 85085-75-2, 85085-76-3, 85085-76-3, 85116-63-8, 85136-05-6, 85136-06-7, 85136-07-8, 85136-08-9, 85136-10-3, 85180-66-1, 85203-56-1, 85203-56-1, 85232-76-4, 85251-63-4, 85251-63-4, 85251-66-7, 85251-67-8, 85251-67-8, 85351-07-1, 85409-36-5, 85480-32-6, 85480-33-7, 85480-33-7, 85480-33-7, 85480-37-1, 85480-37-1, 85480-37-1, 85480-47-3, 85507-69-3, 85507-69-3, 85508-08-3, 85536-25-0, 85554-64-9, 85554-69-4, 85554-72-9, 85586-66-9, 85586-67-0, 85665-35-6, 85940-29-0, 85940-29-0, 85940-31-4, 85940-31-4, 85940-31-4, 85940-32-5, 85940-32-5, 85940-32-5, 85940-38-1, 85960-81-2, 86115-11-9, 86198-35-8, 87061-04-9, 87118-95-4, 87641-24-5, 87731-18-8, 89957-44-8, 89957-63-1, 89957-91-5, 89957-91-5, 89957-91-5, 89957-91-5, 89957-91-5, 89957-93-7, 89957-97-1, 89957-98-2, 89957-98-2, 89957-98-2, 89957-99-3, 89957-99-3, 89958-10-1, 89958-29-2, 89958-29-2, 89958-29-2, 89958-30-5, 89958-31-6, 89958-31-6, 89997-33-1, 89997-34-2, 89997-34-2, 89997-34-2, 89997-35-3, 89997-35-3, 89997-35-3, 89997-35-3, 89997-35-3, 89997-47-7, 89997-53-5, 89997-56-8, 89997-56-8, 89997-63-7, 89997-74-0, 89997-74-0, 89997-74-0, 89997-74-0, 89997-88-6, 89997-88-6, 89997-96-6, 89998-01-6, 89998-14-1, 89998-14-1, 89998-14-1, 89998-14-1, 89998-14-1, 89998-14-1, 89998-15-2, 89998-16-3, 90028-03-8, 90028-03-8, 90028-03-8, 90028-06-1, 90028-36-7, 90028-36-7, 90028-38-9, 90028-48-1, 90028-48-1, 90028-67-4, 90028-67-4, 90028-68-5, 90028-68-5, 90028-70-9, 90028-70-9, 90028-76-5, 90028-76-5, 90028-76-5, 90028-76-5, 90028-83-4, 90028-83-4, 90045-28-6, 90045-36-6, 90045-38-8, 90045-43-5, 90045-43-5, 90045-43-5, 90045-43-5, 90045-43-5, 90045-43-5, 90045-43-5, 90045-43-5, 90045-43-5, 90045-46-8, 90045-53-7, 90045-56-0, 90045-56-0, 90045-56-0, 90045-62-8, 90045-89-9, 90045-89-9, 90045-89-9, 90045-89-9, 90045-90-2, 90045-90-2, 90045-91-3, 90045-94-6, 90045-94-6, 90045-94-6, 90046-02-9, 90046-02-9, 90046-02-9, 90046-02-9, 90046-02-9, 90046-03-0, 90046-17-6, 90046-17-6, 90046-17-6, 90046-17-6, 90046-17-6, 90063-37-9, 90063-37-9, 90063-37-9, 90063-37-9, 90063-37-9, 90063-37-9, 90063-37-9, 90063-37-9, 90063-37-9, 90063-38-0, 90063-52-8, 90063-52-8, 90063-52-8, 90063-53-9, 90063-53-9, 90063-55-1, 90063-56-2, 90063-59-5, 90063-63-1, 90063-63-1, 90063-63-1, 90063-63-1, 90063-63-1, 90063-85-7, 90063-86-8, 90063-97-1, 90063-97-1, 90064-00-9, 90064-00-9, 90064-09-8, 90064-24-7, 90064-25-8, 90064-25-8, 90064-26-9, 90064-26-9, 90064-27-0, 90064-28-1, 90064-32-7, 90064-32-7, 90064-32-7, 90064-34-9, 90064-34-9, 90064-34-9, 90064-35-0, 90082-13-6, 90082-13-6, 90082-23-8, 90082-26-1, 90082-43-2, 90082-43-2, 90082-43-2, 90082-45-4, 90082-46-5, 90082-46-5, 90082-46-5, 90082-46-5, 90082-51-2, 90082-51-2, 90082-51-2, 90082-51-2, 90082-51-2, 90082-51-2, 90082-55-6, 90082-55-6, 90082-55-6, 90082-55-6, 90082-59-0, 90082-60-3, 90082-60-3, 90082-60-3, 90082-60-3, 90082-61-4, 90082-61-4, 90082-72-7, 90082-73-8, 90082-74-9, 90082-74-9, 90082-75-0, 90082-75-0, 90082-77-2, 90082-77-2, 90082-82-9, 90082-82-9, 90106-03-9, 90106-03-9, 90106-21-1, 90106-38-0, 90106-38-0, 90106-38-0, 90106-38-0, 90106-38-0, 90106-49-3, 90106-49-3, 90106-49-3, 90106-54-0, 90106-68-6, 90131-10-5, 90131-10-5, 90131-21-8, 90131-24-1, 90131-25-2, 90131-36-5, 90131-43-4, 90131-45-6, 90131-45-6, 90131-58-1, 90131-58-1, 90131-58-1, 90131-59-2, 90131-63-8, 90131-63-8, 90131-63-8, 90131-83-2, 90131-83-2, 90131-89-8, 90147-36-7, 90147-36-7, 90147-36-7, 90147-36-7, 90147-36-7, 90147-36-7, 90147-36-7, 90147-36-7, 90244-89-6, 90244-99-8, 90320-35-7, 90320-35-7, 90320-37-9, 90320-42-6, 90320-42-6, 90320-49-3, 90397-38-9, 90411-73-7, 90480-35-6, 90480-40-3, 90530-04-4, 90604-30-1, 90622-57-4, 90622-58-5, 90622-72-3, 90989-95-0, 90990-04-8, 91052-92-5, 91053-31-5, 91053-40-6, 91078-93-2, 91079-33-3, 91080-23-8, 91082-91-6, 91672-23-0, 91697-89-1, 91721-75-4, 91721-75-4, 91721-98-1, 91721-98-1, 91722-18-8, 91722-18-8, 91722-18-8, 91722-19-9, 91722-19-9, 91722-19-9, 91722-29-1, 91722-29-1, 91722-39-3, 91722-39-3, 91722-47-3, 91722-54-2, 91722-54-2, 91722-58-6, 91722-58-6, 91722-61-1, 91722-61-1, 91722-62-2, 91722-65-5, 91722-66-6, 91722-69-9, 91722-69-9, 91722-69-9, 91722-81-5, 91722-83-7, 91722-83-7, 91722-84-8, 91722-84-8, 91722-87-1, 91722-87-1, 91722-87-1, 91722-89-3, 91722-91-7, 91722-93-9, 91723-40-9, 91745-64-1, 91745-85-6, 91745-85-6, 91745-88-9, 91745-89-0, 91745-89-0, 91745-89-0, 91745-89-0, 91745-97-0, 91745-97-0, 91770-11-5, 91770-12-6, 91770-12-6, 91770-14-8, 91770-14-8, 91770-14-8, 91770-14-8, 91770-17-8, 91770-24-0, 91770-38-6, 91770-38-6, 91770-38-6, 91770-47-7, 91770-48-8, 91770-48-8, 91770-56-8, 91770-56-8, 91770-56-8, 91770-56-8, 91770-68-2, 91770-68-2, 91770-69-3, 91770-75-1, 91770-75-1, 91770-83-1, 91770-83-1, 91770-83-1, 91770-88-6, 91770-88-6, 91771-36-7, 91771-36-7, 91771-36-7, 91771-40-3, 91771-47-0, 91771-47-0, 91771-48-1, 91771-48-1, 91771-48-1, 91771-48-1, 91771-48-1, 91771-48-1, 91771-50-5, 91771-50-5, 91771-50-5, 91771-50-5, 91771-52-7, 91771-60-7, 91771-60-7, 91771-61-8, 91771-62-9, 91771-62-9, 91771-65-2, 91771-67-4, 91771-68-5, 91771-68-5, 91771-69-6, 91844-86-9, 91844-86-9, 91844-92-7, 91844-92-7, 91845-22-6, 91845-22-6, 91845-22-6, 91845-26-0, 91845-26-0, 91845-35-1, 91845-48-6, 91845-48-6, 91845-48-6, 91845-53-3, 91845-54-4, 92015-65-1, 92113-09-2, 92113-39-8, 92128-34-2, 92128-34-2, 92128-62-6, 92128-62-6, 92201-48-4, 92201-50-8, 92201-50-8, 92201-55-3, 92201-55-3, 92201-55-3, 92201-56-4, 92201-64-4, 92201-64-4, 92201-74-6, 92201-96-2, 92202-02-3, 92202-

02-3, 92202-04-5, 92202-04-5, 92346-82-2, 92346-85-5, 92346-85-5, 92346-89-9, 92346-89-9, 92346-89-9, 92346-89-9, 92346-89-9, 92346-89-9, 92346-89-9, 92347-02-9, 92347-02-9, 92347-05-2, 92347-05-2, 92347-05-2, 92347-09-6, 92347-13-2, 92347-13-2, 92347-21-2, 92347-25-6, 92347-25-6, 92368-90-6, 92456-63-8, 92456-63-8, 92456-82-1, 92457-16-4, 92457-18-6, 92457-18-6, 92502-71-1, 92585-24-5, 92623-75-1, 92623-76-2, 92623-76-2, 92623-76-2, 92704-01-3, 92704-01-3, 92704-03-5, 92704-03-5, 92704-03-5, 92704-03-5, 92704-03-5, 92704-03-5, 92704-07-9, 92729-55-0, 92874-96-9, 92875-02-0, 92908-29-7, 93062-64-7, 93062-89-6, 93165-00-5, 93165-00-5, 93165-11-8, 93165-11-8, 93165-18-5, 93165-22-1, 93165-22-1, 93165-40-3, 93165-40-3, 93165-40-3, 93165-40-3, 93165-50-5, 93165-50-5, 93334-48-6, 93334-48-6, 93334-56-6, 93348-14-2, 93348-31-3, 93348-49-3, 93384-28-2, 93384-32-8, 93384-32-8, 93384-40-8, 93384-40-8, 93455-95-9, 93455-95-9, 93455-96-0, 93455-97-1, 93572-64-6, 93685-34-8, 93685-55-3, 93685-55-3, 93685-73-5, 93685-73-5, 93685-88-2, 93685-88-2, 93685-96-2, 93685-96-2, 93686-00-1, 93686-22-7, 93686-22-7, 93686-30-7, 93762-34-6, 93763-95-2, 93777-41-4, 93804-64-9, 93804-81-0, 93805-22-2, 93805-72-2, 93840-90-5, 93843-13-1, 93857-93-3, 93882-22-5, 93892-03-6, 93892-04-7, 93892-05-8, 93892-07-0, 93893-89-1, 93894-30-5, 93904-56-4, 93917-67-0, 93919-04-1, 93939-86-7, 93941-67-4, 93941-69-6, 93941-73-2, 93942-00-8, 93952-58-0, 93963-78-1, 93981-50-1, 93981-59-0, 93981-63-6, 94021-42-8, 94021-60-0, 94022-01-2, 94022-02-3, 94022-06-7, 94022-07-8, 94071-12-2, 94087-23-7, 94087-83-9, 94089-01-7, 94089-21-1, 94089-23-3, 94108-09-5, 94109-97-4, 94133-92-3, 94134-03-9, 94159-31-6, 94159-32-7, 94160-12-0, 94167-14-3, 94200-10-9, 94200-11-0, 94201-19-1, 94201-28-2, 94201-73-7, 94248-21-2, 94248-38-1, 94265-97-1, 94265-98-2, 94265-99-3, 94266-43-0, 94266-45-2, 94266-47-4, 94266-47-4, 94266-48-5, 94266-48-5, 94266-48-5, 94266-48-5, 94278-39-4, 94279-82-0, 94279-84-2, 94280-15-6, 94291-50-6, 94333-50-3, 94333-69-4, 94333-73-0, 94333-75-2, 94333-77-4, 94333-78-5, 94333-88-7, 94333-91-2, 94333-91-2, 94333-93-4, 94333-96-7, 94333-99-0, 94333-99-0, 94333-99-0, 94333-99-0, 94333-99-0, 94334-02-8, 94334-04-0, 94334-06-2, 94334-11-9, 94334-12-0, 94334-13-1, 94334-14-2, 94334-25-5, 94334-26-6, 94334-32-4, 94334-32-4, 94334-35-7, 94334-35-7, 94334-35-7, 94334-53-9, 94349-73-2, 94350-02-4, 94350-02-4, 94350-02-4, 94350-02-4, 94350-09-1, 94350-09-1, 94386-39-7, 94386-48-8, 94406-01-6, 94406-15-2, 94465-76-6, 94891-25-5, 94891-27-7, 94891-27-7, 94891-27-7, 94891-27-7, 94891-27-7, 94891-28-8, 95009-46-4, 95009-46-4, 96507-91-4, 96507-91-4, 96682-10-9, 97231-35-1, 97281-55-5, 97358-54-8, 97358-55-9, 97384-48-0, 97404-53-0, 97404-53-0, 97435-14-8, 97435-14-8, 97553-36-1, 97553-37-2, 97593-06-1, 97593-29-8, 97593-51-6, 97659-55-7, 97659-68-2, 97659-70-6, 97659-70-6, 97660-07-6, 97660-07-6, 97675-63-3, 97675-68-8, 97675-74-6, 97676-05-6, 97676-05-6, 97676-05-6, 97676-05-6, 97676-05-6, 97676-09-0, 97676-13-6, 97676-19-2, 97676-22-7, 97676-22-7, 97676-22-7, 97676-22-7, 97722-12-8, 97722-12-8, 97722-12-8, 97752-28-8, 97766-30-8, 97766-30-8, 97766-30-8, 97766-30-8, 97766-30-8, 97926-19-7, 97926-23-3, 97926-41-5, 97926-41-5, 97926-74-4, 97926-84-6, 97927-02-1, 97952-61-9, 97952-71-1, 97952-72-2, 97952-72-2, 97952-72-2, 97952-72-2, 97952-72-2, 97952-72-2, 97952-72-2, 97952-72-2, 98084-79-8, 98306-02-6, 98314-98-8, 98561-44-5, 98561-44-5, 98653-81-7, 98653-81-7, 98653-81-7, 98903-76-5, 98903-76-5, 99098-35-8, 99811-75-3, 99886-27-8, 99948-88-6, 100084-96-6, 100209-23-2, 100209-32-3, 100209-33-4, 100298-95-1, 101426-31-7, 102242-62-6, 102322-83-8, 103694-68-4, 104468-21-5, 104986-28-9, 106232-83-1, 111850-00-1, 111879-80-2, 113486-29-6, 114099-96-6, 114119-97-0, 115422-59-8, 116963-97-4, 118562-73-5, 121199-28-8, 121432-33-5, 122760-84-3, 122760-85-4, 122795-41-9, 122861-78-3, 125109-85-5, 125352-06-9, 127248-84-4, 127931-21-9, 128119-70-0, 128489-04-3, 129316-65-0, 131766-73-9, 131812-67-4, 134123-93-6, 136954-20-6, 136954-25-1, 139504-68-0, 139539-66-5, 139564-42-4, 141773-73-1, 142653-61-0, 153175-57-6, 154171-76-3, 156472-94-5, 163266-17-9, 165191-91-3, 166301-21-9, 169054-69-7, 170678-49-6, 180964-47-0, 188417-26-7, 188570-78-7, 196109-18-9, 198404-98-7, 203719-53-3, 203719-54-4, 207801-32-9, 211241-68-8, 211323-05-6, 220621-22-7, 223749-05-1, 233665-90-2, 233665-96-8, 233666-04-1, 253596-70-2, 292605-05-1, 324742-96-3, 338735-71-0, 365411-50-3, 400052-49-5, 437770-28-0, 444085-42-1, 478695-70-4, 479547-57-4, 648434-55-3, 723759-62-4, 831213-72-0, 850309-45-4, 851768-51-9, 852997-28-5, 871465-49-5, 888021-82-7, 891781-90-1, 896447-13-5, 923593-56-0, 923593-57-1, 929116-08-5, 930587-76-1, 977017-81-4, 977017-82-5, 977018-53-3, 977029-66-5, 977029-68-7, 977060-66-4, 977075-23-2, 977091-83-0, 977185-29-7, 984650-63-5, 1048028-77-8, 1048028-77-8, 1064678-08-5, 1174331-46-4, 1192738-48-9, and 1271488-66-4.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for releasing flavor, the system comprising:
a plurality of compartments adapted to each receive one of a respective plurality of capsules, each capsule containing therein a flavor material;
a dispenser system configured for dispensing into an environment a fluid obtained from at least one flavor material; and
a controller configured for automatically selecting a dispensing protocol from a list of dispensing protocols, for signaling said dispenser system to dispense fluids obtained from at least one flavor material contained in at least one capsule of said compartments, and for automatically re-executing said selecting and said signaling, according to a shuffle protocol which includes probabilities for selecting said dispensing protocol;
a remote user interface; and
a communication system configured for communicating with said remote user interface;
wherein said remote user interface is configured for allowing a user to select said shuffle protocol by presenting a list of available shuffle protocols, or to select parameters for said shuffle protocol, said parameters being selected from the group consisting of compartment selection probabilities, mixing ratio selection probabilities, and time intervals between successive selections.

2. The system according to claim 1, wherein said controller is configured to extract information pertaining to contents of capsules in said containers, and automatically selecting said protocol based on said information.

3. The system according to claim 1, wherein said controller is configured for shuffling between dispensing activities with a higher dispensing rate and dispensing activities with a lower dispensing rate.

4. The system according to claim 1, wherein said controller is configured for shuffling between dispensing activities with a higher duration and dispensing activities with a lower duration.

5. The system according to claim 1, wherein said controller is configured for shuffling between dispensing activities with longer pauses between dispensing events and dispensing activities with shorter pauses between dispensing events.

6. The system according to claim 1, wherein said controller is configured for shuffling between mixing ratios, and to control, for each mixing ratio, relative amounts of fluids dispensed from at least two capsules, responsively to said mixing ratio.

7. The system according to claim 1, wherein said controller is configured for automatically selecting a compartment according to said shuffle protocol, and for signaling said dispenser system to dispense fluids obtained from flavor materials contained in a capsule of said selected compartment.

8. The system according to claim 1, wherein said controller is configured for automatically selecting at least two compartments according to said shuffle protocol, and for signaling said dispenser system to dispense fluids obtained from flavor materials contained in capsules of said at least two selected compartments.

9. The system according to claim 1, wherein said dispenser system comprises a plurality of dispensing elements and wherein said controller signals each dispensing element to dispense a fluid obtained from a flavor material contained in a different capsule.

10. The system according to claim 1, wherein said dispenser system comprises at least one fluid channel forming fluid communication between a respective compartment and said environment, wherein said controller is configured for opening and blocking said at least one fluid channel, thereby to establish or prevent said fluid communication.

11. The system according to claim 1, further comprising a mixing chamber, wherein said dispenser system comprises at least one fluid channel forming fluid communication between a respective compartment and said mixing chamber, and wherein said controller is configured for opening and blocking said at least one fluid channel, thereby to establish or prevent said fluid communication.

12. The system according to claim 1, further comprising a user interface configured for at least one of (i) activating said controller and/or said dispenser system, (ii) deactivating said controller and/or said dispenser system, and (iii) entering selection data indicating which of the capsules is to be active.

13. The system according to claim 1, wherein said dispenser system comprises a blower or a fan.

14. The system according to claim 1, wherein at least one of said capsules contains said flavor material in a liquid state at room temperature.

15. The system according to claim 1, wherein at least one of said capsules contains said flavor material in a gaseous state at room temperature.

16. The system according to claim 1, wherein said flavor material in at least one of said capsules is a scent material.

17. A method of releasing a flavor into an environment, comprising loading into the system according to claim 1 a plurality of capsules, each containing therein a flavor material, and activating the system to dispense a fluid obtained from a flavor material contained in at least one of said capsules.

18. The method of claim 17, wherein the environment is selected from the group consisting of a living room, a bedroom, a kitchen, a lavatory, a hotel room, a lobby, a waiting room, an office, a restaurant, a massage parlor and a vehicle.

* * * * *

UNITED STATES PATENT AND TRADEMARK OFFICE
CERTIFICATE OF CORRECTION

PATENT NO. : 11,083,813 B2
APPLICATION NO. : 16/615430
DATED : August 10, 2021
INVENTOR(S) : Yoav Avidor Page 1 of 1

It is certified that error appears in the above-identified patent and that said Letters Patent is hereby corrected as shown below:

On the Title Page

Item (73) Assignee:
"Agaa Aroma & fine chemicals Ltd."
Should be changed to:
-- Agan Aroma & fine chemicals Ltd. --

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*